US012790244B2

(12) United States Patent
Tokhtuev et al.

(10) Patent No.: US 12,790,244 B2
(45) Date of Patent: Nov. 10, 2026

(54) METHOD AND DEVICE FOR MONITORING CHLORINE IN A POOL

(71) Applicant: Ecolab USA Inc., St. Paul, MN (US)

(72) Inventors: Eugene Tokhtuev, Woodbury, MN (US); Anatoly Skirda, Eagan, MN (US); Michael Patrick Kremer, Rosemount, MN (US); Michael Grieger, St. Paul, MN (US)

(73) Assignee: Ecolab USA Inc., St. Paul, MN (US)

(*) Notice: Subject to any disclaimer, the term of this patent is extended or adjusted under 35 U.S.C. 154(b) by 370 days.

(21) Appl. No.: 18/405,173

(22) Filed: Jan. 5, 2024

(65) Prior Publication Data

US 2025/0223205 A1 Jul. 10, 2025

(51) Int. Cl.

*C02F 1/66* (2023.01)
*C02F 1/00* (2023.01)
(Continued)

(52) U.S. Cl.

CPC .............. *C02F 1/686* (2013.01); *C02F 1/001* (2013.01); *C02F 1/008* (2013.01); *C02F 1/66* (2013.01);
(Continued)

(58) Field of Classification Search

CPC .......... C02F 1/686; C02F 1/001; C02F 1/008; C02F 1/66; C02F 1/76; C02F 2103/42; C02F 2209/06; C02F 2209/29; C02F 2301/046; C02F 2303/04; C02F 1/32; C02F 2201/3222; C02F 2209/001; C02F 2209/003; C02F 2209/005; C02F 2209/11; G01N 21/59; G01N 33/182; E04H 4/12; E04H 4/1209; E04H 4/1281

See application file for complete search history.

(56) References Cited

U.S. PATENT DOCUMENTS

| | | | |
|---|---|---|---|
| 4,176,031 | A | 11/1979 | Rosenblum |
| 4,917,868 | A | 4/1990 | Alexander et al. |

(Continued)

FOREIGN PATENT DOCUMENTS

| | | | | |
|---|---|---|---|---|
| KR | 20170142604 A | * 12/2017 | ............. | G01N 21/33 |
| KR | 102187534 B1 | * 12/2020 | .............. | C02F 1/008 |

(Continued)

OTHER PUBLICATIONS

Escapenet Machine Translation of PT1882178E, Mar. 14, 2012. (Year: 2012).*

(Continued)

*Primary Examiner* — Joseph W Drodge

(74) *Attorney, Agent, or Firm* — Fredrikson & Byron, P.A.

(57) ABSTRACT

Systems and methods for monitoring, controlling, and maintaining the quality of water in swimming pools. An optical sensor for determining a concentration of a concentrated chlorine solution of a feeder system for a swimming pool. A method including measuring a concentration of a sanitization element in a feeder tank for a swimming pool, and using the measured concentration to control a concentration of the sanitization element in a swimming pool volume tank, the method implemented by one or more processors operatively coupled to a non-transitory computer readable storage device, on which modules of instruction code are stored.

20 Claims, 21 Drawing Sheets

(51) Int. Cl.

| | |
|---|---|
| ***C02F 1/68*** | (2023.01) |
| ***C02F 1/76*** | (2023.01) |
| ***E04H 4/12*** | (2006.01) |
| ***G01N 21/59*** | (2006.01) |
| ***G01N 33/18*** | (2006.01) |
| *C02F 103/42* | (2006.01) |

(52) U.S. Cl.

CPC ............. *C02F 1/76* (2013.01); *E04H 4/1281* (2013.01); *G01N 21/59* (2013.01); *G01N 33/182* (2013.01); *C02F 2103/42* (2013.01); *C02F 2209/06* (2013.01); *C02F 2209/29* (2013.01); *C02F 2301/046* (2013.01); *C02F 2303/04* (2013.01)

(56) References Cited

U.S. PATENT DOCUMENTS

| | | | | | |
|---|---|---|---|---|---|
| 5,422,014 | A * | 6/1995 | Allen | C02F 1/008 | 210/743 |
| 5,616,239 | A * | 4/1997 | Wendell | B01D 37/02 | 210/167.13 |
| 5,662,795 | A | 9/1997 | Pickens et al. | | |
| 6,881,583 | B2 | 4/2005 | Kahle | | |
| 7,372,039 | B2 | 5/2008 | Tokhtuev et al. | | |
| 7,402,252 | B2 | 7/2008 | Kadlec et al. | | |
| 7,569,150 | B2 | 8/2009 | Kilawee et al. | | |
| 7,639,361 | B2 | 12/2009 | Shakespeare et al. | | |
| 7,736,522 | B2 | 6/2010 | Kilawee et al. | | |
| 7,883,622 | B1 * | 2/2011 | Barnes | E04H 4/1209 | 210/206 |
| 8,212,222 | B2 | 7/2012 | Shakespeare et al. | | |
| 8,968,660 | B2 | 3/2015 | Davis et al. | | |
| 9,791,429 | B2 | 10/2017 | Howes, Jr. et al. | | |
| 9,829,475 | B2 | 11/2017 | Howes, Jr. et al. | | |
| 10,155,679 | B2 | 12/2018 | Mastio | | |
| 10,371,685 | B2 | 8/2019 | Laflamme et al. | | |
| 10,604,954 | B2 | 3/2020 | Shalon et al. | | |
| 11,162,272 | B2 | 11/2021 | Shalon et al. | | |
| 11,286,177 | B2 | 3/2022 | Yizhack et al. | | |
| 2002/0144958 | A1 * | 10/2002 | Sherman | C02F 1/505 | 210/764 |
| 2007/0090059 | A1 * | 4/2007 | Plummer | G05B 23/0235 | 210/743 |
| 2008/0285011 | A1 * | 11/2008 | Shakespeare | G01N 21/33 | 356/326 |
| 2009/0212236 | A1 * | 8/2009 | Tokhtuev | G01N 21/6402 | 250/564 |
| 2010/0206787 | A1 * | 8/2010 | Rozenberg | G01N 21/33 | 210/96.1 |
| 2013/0313204 | A1 | 11/2013 | Shalon et al. | | |
| 2014/0144849 | A1 | 5/2014 | Wojtaszczyk | | |
| 2016/0299096 | A1 * | 10/2016 | Greenwood | C02F 1/66 | |
| 2020/0369534 | A1 * | 11/2020 | Kleiber | C02F 1/008 | |
| 2025/0011191 | A1 * | 1/2025 | Martin | C02F 1/008 | |
| 2025/0223205 | A1 * | 7/2025 | Tokhtuev | C02F 1/66 | |

FOREIGN PATENT DOCUMENTS

| | | | | | |
|---|---|---|---|---|---|
| PT | 1882178 | E * | 3/2012 | G01N 21/7703 |
| WO | 2021216347 | A1 | 10/2021 | |

OTHER PUBLICATIONS

Escapenet Machine Translation of KR20170142604, Dec. 28, 2017. (Year: 2017).*

Escapenet machine translation of KR-102187534-B1, Dec. 7, 2020. (Year: 2020).*

Boris Obrovski et al, “Modernized sensor measurement technique for determination of chlorine in bathing water”. International Journal of Environmental Science and Technology (2022) 19: pp. 11673-11684. (Year: 2022).*

International Searching Authority, “International Search Report and Written Opinion”, From Application No. PCT/US2025/010112, Mailed Mar. 28, 2025, pp. 13.

* cited by examiner

METHOD AND DEVICE FOR MONITORING CHLORINE IN A POOL

TECHNICAL FIELD

The present disclosure relates generally to water quality control and monitoring, and more specifically, to the monitoring and control of sanitization chemical levels in swimming pool water.

BACKGROUND

For effective pool sanitation, it is recommended to maintain a chlorine concentration of approximately 4 parts per million (ppm) in the main pool volume tank of pool water. Frequent or continuous monitoring of chlorine levels in pool water may help to ensure the desired chlorine concentration is maintained. A chlorine concentration of approximately 4 ppm has been found to provide a sufficient amount of disinfection/sanitization, while also ensuring a safe, comfortable swimming environment.

A pool feeder tank or feeder system is designed to prepare a concentrated chlorine solution of calcium hypochlorite, typically around 200 ppm, for use in controlling the chlorine level in the swimming pool. A feeder pump associated with the feeder tank is operated or actuated to direct or dispense the concentrated calcium hypochlorite solution into the main pool recirculation stream, where it is mixed and diluted by the volume of pool water. Water mixing (e.g., between the concentrated feeder tank solution and the larger body of pool water) continues, resulting in a gradual increase in the chlorine concentration in the pool water. The aim is to achieve and/or maintain a chlorine concentration of approximately 4 ppm in the pool water.

Improved systems and methods for monitoring and controlling the chlorine concentration of pool water are needed to ensure adequate sanitization while ensuring a safe swimming environment.

SUMMARY OF THE INVENTION

To monitor, control, and maintain a desired chlorine concentration in a swimming pool, embodiments of this disclosure propose to measure the chlorine concentration associated with the feeder tank (e.g., within the feeder tank, or at the output or downstream of the feeder pump, for example). By measuring the chlorine concentration associated with the feeder tank, proactive adjustments can be made to a number of system settings associated with the pool water recirculation and/or conditioning system and/or with the feeder tank system, such as the main recirculation pump flow rate, or the feeder pump flow rate, or the run time (or "on time") of the feeder pump, or valve positions, or sensor settings, or other system or pool settings, as necessary. Also disclosed herein is a proposed ultraviolet ("UV") sensor that is configured to measure and/or monitor the chlorine concentration associated with the feeder tank to help ensure consistent and accurate monitoring of feeder tank chlorine concentration, and to thereby improve the dosing and control of the chlorine concentration in an associated swimming pool.

DETAILED DESCRIPTION

Figure 1A:
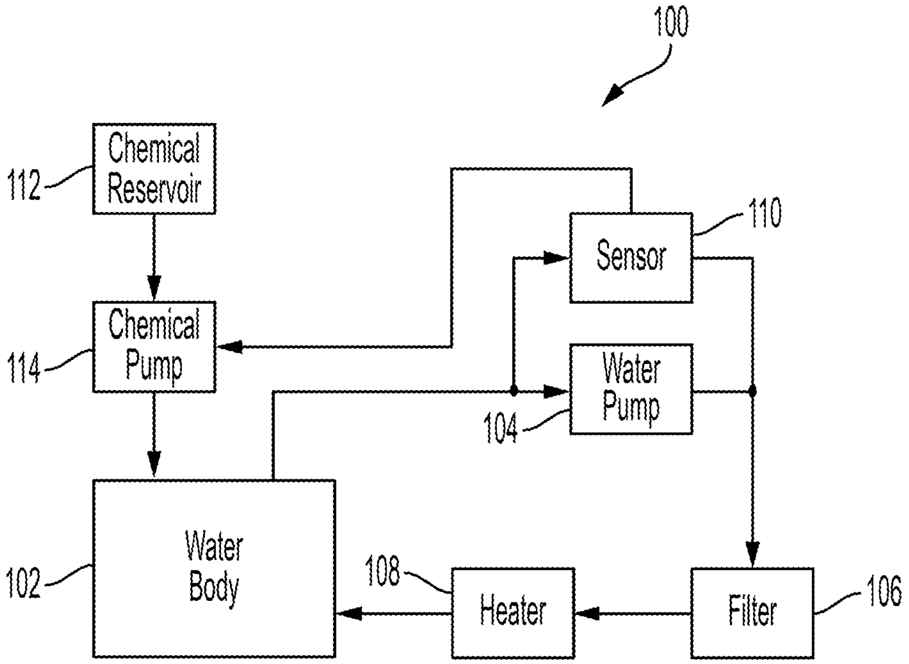
FIG. 1A PRIOR ART
FIGS. 1A and 1B are block diagrams showing two typical arrangements of components of a system for maintaining water conditions or quality in a swimming pool.

Swimming pools are commonly operated using a series of pumps, valves, filters, and/or chemical systems to ensure that the water in the swimming pool is safe and comfortable for human use. Swimming pools are typically made up of a number of common components, each of which is described briefly below, with reference to FIGS. 1A and/or 1B, where applicable:

- Pool Volume Tank: The pool volume tank 102, also known as the pool basin or pool shell, is the main structure that holds most of the pool water of the swimming pool system 100. The pool volume tank holds the body of pool water for swimming and/or recreation purposes;
- Main Pump: The main pump 104 circulates the pool water, pulling or drawing it from the pool volume tank 102 and moving it through a recirculation loop, which often includes a filter or filtration system, before returning it to the pool volume tank 102, for example. The main pump (or main recirculation pump) 104 provides water circulation and facilitates the process of water filtration and/or other treatment of the pool water.
- Filter: The filter 106 removes impurities and debris from the pool water. Filter 106 helps maintain water clarity and quality by trapping or removing particles/particulates and other contaminants from the pool water. The pool water in the recirculation loop passes through the filter 106, which can be a sand filter, cartridge filter, or a diatomaceous earth (DE) filter, as possible examples.
- Heater: A pool heater 108 is an optional component that can be installed to regulate the temperature of the pool water. If a heater 108 is installed, the pool water can be heated as it passes through the heater unit as part of the recirculation loop. The heater can be operated as needed to maintain the water temperature in a desired range, for example, set by the user. It can provide for a more comfortable swimming experience even in cooler weather conditions, for example. For most aquatic activities, the American Red Cross and the National Pool and Spa Institute recommend maintaining swimming pool water in a temperature range of between about 28° C. and 30° C., while spas typically have a temperature range of from about 36° C. to 40° C.
- Sensor Manifold: The sensor or sensor manifold 110 may include a number of different types of sensors configured to monitor different aspects or parameters of the pool water in the pool volume tank 102, such as the water temperature, pH level, oxidation-reduction potential ("ORP") level, chlorine level, the amount or concentration of particulates/dissolved solids, water flow rate, etc. These sensors of the sensor manifold 110 can provide valuable information useful for maintaining safe, healthy conditions of the pool water (e.g., chemical balance) and/or improving pool water conditions/quality. For example, the chlorine level (or concentration) in the pool volume tank 102 is typically monitored by the sensor manifold 110 with a "PPM sensor" such as that described in U.S. Pat. No. 9,829,475, entitled "PPM pool sensor," relevant portions of which are incorporated by reference herein. The various sensor readings at the sensor manifold 110 may be transmitted to a controller, for example, thereby allowing for real-time monitoring and control of various pool water parameters, such as chlorine concentration, for example.
- Calcium Hypochlorite Feeder System: The calcium hypochlorite feeder system (or chlorine feeder system) may include a reservoir or tank system 112 that is fluidly connected to the swimming pool system 100. The chlorine feeder system is typically connected to the main recirculation loop of the pool system 100. This allows the concentrated chlorine solution of the feeder tank 112 to be introduced into the pool water as it circulates through the system 100 prior to returning to the pool volume tank 102. The calcium hypochlorite feeder tank 112 may be a chemical reservoir 112 designed to dispense a relatively concentrated chlorine solution into the pool water via a chemical pump or feeder pump 114 to thereby achieve or maintain a desired chlorine concentration of the pool water in the pool volume tank 102. The concentrated chlorine solution in the feeder tank 112 is typically maintained at a concentration of approximately 200 ppm chlorine. By comparison, the desired concentration of chlorine in the pool water of the pool volume tank 102 is typically about 4 ppm chlorine.

The concentrated chlorine solution in the feeder tank 112 is typically prepared by dilution of calcium hypochlorite tablets, loaded in a top feeder housing. An input line (not shown in FIGS. 1A and 1B) may provide water from the main circulation line to the feeder tank 112. A float valve inside of the feeder tank 112 may, for example, be configured to actuate and spray water on the calcium hypochlorite tablets when the solution level is low; likewise, the float valve may be configured to actuate and stop spraying water when the feeder tank is full (e.g., above a predetermined level). The spraying of water into feeder tank 112 and onto the calcium hypochlorite tablets may start again when the feeder pump 114 is activated and the level of concentrated chlorine solution in the feeder tank 112 drops. Various parameters, such as the number of calcium hypochlorite tablets, the rate of flow in the input line, the distance from the spray nozzle to the tablets, etc., are selected to achieve and maintain the chlorine concentration at approximately 200 ppm chlorine. In some embodiments, the output of feeder pump 114 is connected to the main recirculation loop, for example as shown in FIG. 1B. In some embodiments, a relatively small portion of the concentrated chlorine solution from the output of the feeder pump 114 may be returned to the feeder tank 112. In such embodiments, when the feeder pump 114 is activated, the concentrated chlorine solution that is returned to the feeder tank 112 creates a vortex in the tank 112, thereby mixing the prepared solution and improving the stability of the dispensed solution.

In some embodiments, the calcium hypochlorite feeder system may be programmed to dispense the concentrated chlorine solution periodically into the pool water. The frequency and duration of dispensing can be adjusted based on factors such as pool usage, weather conditions, and chlorine demand. Periodic dispensing of the concentrated chlorine solution may, for example, help to maintain the desired chlorine level in the pool water. The system typically aims to keep the chlorine concentration of the pool water of the pool volume tank 102 near 4 ppm, which is commonly recommended for effective pool sanitation. As the concentrated chlorine solution is introduced into the pool water, it typically undergoes dilution and mixing in the pool water recirculation loop. The pool water and the added concentrated chlorine solution may blend together, thereby resulting in a more uniform distribution of chlorine throughout the pool water system 100.

In embodiments of this disclosure, a proposed UV chlorine sensor is used to monitor the concentration of the chlorine solution associated with the calcium hypochlorite feeder tank 112; this may allow for a system controller (described further below) to adjust or control the addition/dispensing of the concentrated chlorine solution to the pool water (e.g., to adjust the timing of adding the concentrated chlorine solution, or to adjust the flow rate at which the concentrated chlorine solution is added, or the duration of time the concentrated chlorine solution is dispensed, etc.). The use of a UV chlorine sensor and controller according to this disclosure may help to ensure effective pool sanitation/disinfection and may help to maintain a desired, stable chlorine level in the pool water.

It should be noted that the proposed UV chlorine sensor of this disclosure may employ a different mechanism for sensing chlorine concentration than that employed in the chlorine sensor of the sensor manifold 110. For example, the chlorine sensor of the sensor manifold 110 may employ an electrochemical sensing technology, which may provide reliable, accurate results at the relatively low chlorine concentrations typically expected of the pool water of the pool volume tank 102 (e.g., 4-5 ppm chlorine). However, exposure of this type of chlorine sensor to the much higher chlorine concentrations associated with the chlorine feeder tank 112 would result in saturation of the sensor and would likely damage the sensor. The proposed UV chlorine sensor of this disclosure uses an optical sensing technology to measure the high chlorine concentration of the concentrated chlorine solution associated with the chlorine feeder tank 112; it does this by detecting the absorbance of light energy at certain wavelengths of light that correlate well with chlorine concentration in the ranges of interest. This is described in more detail below.

Other aspects of a system for controlling and maintaining water conditions in a swimming pool (not necessarily depicted in FIG. 1A or 1B) may include one or more of the following components:

Acid Pump: An acid pump may be used in conjunction with a swimming pool water monitoring and control system 100 to regulate the pH level of the pool water. The acid pump may be configured to add an amount of an acidic solution into the pool water as part of the recirculation loop to achieve and/or maintain the pH of the pool water within a desired range, for example. The pH level may be monitored by a pH sensor (e.g., as part of the sensor manifold 110), and a controller may adjust the operation of the acid pump according to pH sensor data received from the sensor manifold 110.

Controller: A controller may be implemented in system 100 to serve as the central command unit for the swimming pool system 100. The controller may facilitate and/or coordinate the monitoring and control of various pool functions, such as pump operation, valve positions, heater settings, and sensor operations/readings. The controller may enable automatic control of these functions, and may also be configured to provide an interface for a user to adjust and maintain the pool water conditions manually, for example.

Reference is made again to FIGS. 1A and 1B, which show exemplary block diagrams of a system 100 for controlling water parameters or quality in a water body 102. The system 100 of FIGS. 1A and 1B includes a water body 102, such as a pool or spa, which is intended to be maintained/treated. The system 100 can include a main water pump 104 for circulating water through a water recirculation loop, which may include various components of the system 100. For example, in the illustrated system 100 of FIGS. 1A and 1B, the water pump 104 is configured to circulate pool water drawn from pool volume tank or water body 102 and move the pool water through a filter 106 and an optional heater 108 before returning the pool water to the water body 102. Often, the water body 102 is treated with one or more chemicals, which can be stored in one or more chemical reservoirs 112, and incorporated into the pool water of the water body 102 via one or more chemical pumps 114. Exemplary chemicals to be added to the water can include chlorine solutions and/or acidic chemicals for maintaining a desired chemistry in the pool water of water body 102.

Figure 1B:
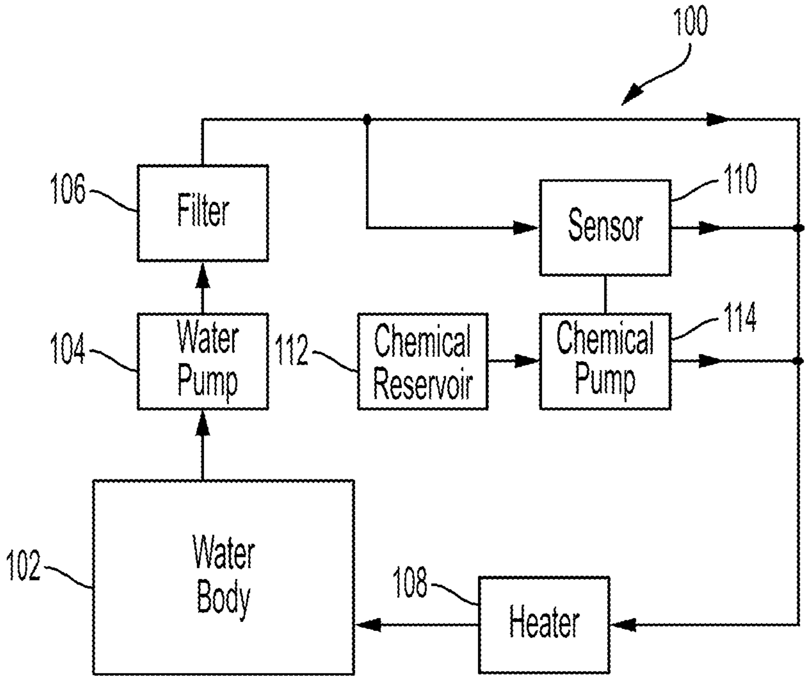
FIG. 1B PRIOR ART

In some systems, a sensor or sensor manifold 110 can be positioned in system 100 (e.g., in a recirculation loop with the water pump 104) so that the sensor 110 receives at least a portion of the pool water pumped by the water pump 104, as shown in FIGS. 1A and 1B. In some cases, the sensor 110 can be placed in series with the water pump 104; in such cases, the sensor 110 may receive all of the fluid flowing through the water circulation loop, for example. In FIG. 1A, the sensor 110 is shown positioned in parallel with the water pump 104 and is configured to receive only a portion of the pool water being pumped by water pump 104. In various other possible examples, the sensor 110 could alternatively be positioned in parallel with any other part of the recirculation loop and thereby receive a portion of the pool water that flows through the loop, for example as shown in FIG. 1B. Some systems 100 can include an arrangement of valves to control the flow of pool water to the sensor 110 from the water recirculation loop.

In some systems, the sensor manifold 110 may be in communication with one or more chemical pumps 114. The one or more chemical pumps 114 can be configured to dispense one or more corresponding chemicals or chemical solutions from respective chemical reservoirs 112 into the pool water of the recirculation loop (e.g., to be added to the pool water of the pool volume tank 102). FIG. 1A shows an example system 100 in which chemicals from a chemical reservoir 112 are dispensed into water body 102; however, in some implementations, such as the one depicted in FIG. 1B, it may be preferable to dispense the chemical into a portion of the water circulation loop in order to facilitate some amount of mixing of the chemical with the water in the water recirculation loop prior to being added directly to water body 102. The sensor 110 may be used to control the addition of one or more chemicals from a chemical reservoir 112 to the water body 102 (e.g., via the recirculation loop) based on one or more parameters sensed by the sensor or sensors 110. For example, in the event that the sensor manifold 110 detects a level of a particular chemical (e.g., chlorine) that is below a desired level (e.g., below a predetermined threshold level), a signal from the sensor manifold 110 can be used to cause the chemical pump 114 to run in order to dose (e.g., dispense or add) the chemical from the chemical reservoir 112 into the water body 102 (or into the recirculation loop prior to delivery to the pool volume tank 102) in order to raise the level of the chemical towards the desired level.

With continued reference to FIGS. 1A and 1B, the sensor 110 can be in communication with, for example, a chemical pump 114 configured to dose a chemical from a chemical reservoir 112 into the water body 102 (or into the recirculation loop prior to delivery to the pool volume tank 102). In some examples, the sensor 110 can trigger one or more chemical pumps (e.g., pump 114) to add or dose one or more chemicals into the water body 102 based on data received by a controller or processor associated with system 100. For instance, a controller or processor may receive data from the sensor 110 regarding the chlorine concentration of pool water, and the controller or processor can compare the measured concentration of chlorine in the pool water sample to a threshold concentration, and, in the event that the measured chlorine concentration is below the threshold, the controller or processor can then cause a chemical pump 114 to run to dispense a concentrated chlorine solution from the feeder tank 112 into the water body 102 (e.g., by pumping the solution into the recirculation loop prior to delivery to the pool volume tank 102). Chlorine-sourcing chemicals for generating the concentrated chlorine solution in the feeder tank are generally known and can include, for example, calcium hypochlorite or liquid bleach.

In some examples, data from the sensor 110 received by a controller or processor can cause a chemical pump (e.g., pump 114) to dose or dispense a chemical into the recirculation loop (and from there into the water body 102) based on auxiliary data. For instance, in the event that an auxiliary pH sensor determines that the pH of the water is above a predetermined threshold, the sensor (and/or a processor associated with the sensor) can cause a chemical pump 114 to add an acidic fluid or other pH-lowering chemical (such as muriatic acid) to the pool water to reduce the pH value of the pool water in the water body 102. Various pH-lowering chemicals such as acids can be diluted to various degrees for effecting an appropriate pH change in the pool water of the water body 102. Conversely, if the determined pH is below a predetermined threshold, the sensor data could be used to trigger a chemical pump 114 to add a pH-raising chemical, for example, sodium carbonate. In various examples, the sensor 110 (and/or a processor or controller associated with, or in communication with, the sensor) can further be in communication with the water pump 104 or the heater 108 (or to valves in the system 100) to adjust operation in response to detected auxiliary data such as water flow rate or temperature.

In some examples, the sensor 110 can actively monitor a fluid sample under test (e.g., water from the water body 102) to determine the concentration of a constituent parameter such as chlorine in substantially real time. In some examples, a parameter such as the chlorine concentration, by itself or in combination with any other received auxiliary data, can be used to determine when, and to what extent, to add one or more chemicals to the pool water in order to maintain appropriate parameters thereof, such as chlorine concentration, pH, etc. The measurement of such parameters may allow for frequent, ongoing, and/or real-time control of such parameters of the pool water in the water body 102, such as the chlorine concentration, pH, or other desired parameters. Such real-time control can reduce or eliminate overshoot, over-correction, or under-correction of the water parameters.

In some embodiments, pool water system 100 may operate in cycles based, for example, on user settings and/or pool requirements. In some cases, the main pump 104 may run for a certain duration to circulate the pool water and provide filtration. The heating and pH control functions may be activated as needed, depending on the desired water temperature and PH levels, respectively. One or more algorithms may be employed to dispense concentrated chlorine solution from the chlorine feeder system based on monitoring of chlorine concentration at various points in the system 100 (e.g., within the calcium hypochlorite feeder tank 112, or at the output of the calcium hypochlorite feeder pump 114, or at the sensor manifold 110, or from a combination of these locations) may improve the response time and accuracy of maintaining the chlorine concentration levels in the pool water of the pool volume tank 102 at or near 4 ppm.

Overall, the components of a pool water system 100 according to this disclosure work together to improve any or all of the following: water circulation, filtration, heating, and chemical balance. A controller, along with inputs from the sensor manifold 110 and a UV chlorine sensor of this disclosure, may provide control and monitoring capabilities, which may further enable some level of automatic control and maintenance of pool water conditions.

Additionally, the combination of a calcium hypochlorite feeder system with a UV chlorine sensor of this disclosure, which may be employed in a variety of connections to the pool system 100, may help to ensure that the pool water remains properly sanitized and at a consistent, desired chlorine level for safe and enjoyable experiences by users.

Examples of Use: Pool Fluidic Systems with Monitoring of Concentrated Chlorine Levels in Chlorine Feeder Systems Option A In Option A, a chlorine sensor is connected to the chlorine feeder tank, and a dedicated pump is used to draw concentrated chlorine solution from the chlorine feeder tank, move the concentrated chlorine solution through the chlorine sensor, and then return the concentrated chlorine solution back to the feeder tank. A controller may be configured to receive readings from the chlorine sensor and can use the information to adjust the dispensing time (e.g., the run time of the chlorine feeder pump) as necessary. Additionally, the controller may utilize data about the chlorine concentration in the feeder tank to detect abnormalities in the feeder operation, such as out-of-product events, feeder pump malfunctioning, or clogged lines. The dedicated pump for the chlorine sensor may, in some cases, be activated by the controller to run only if and when such measurements are needed, which may thereby increase the lifespan of the pump and/or the chlorine sensor.

Figure 2:
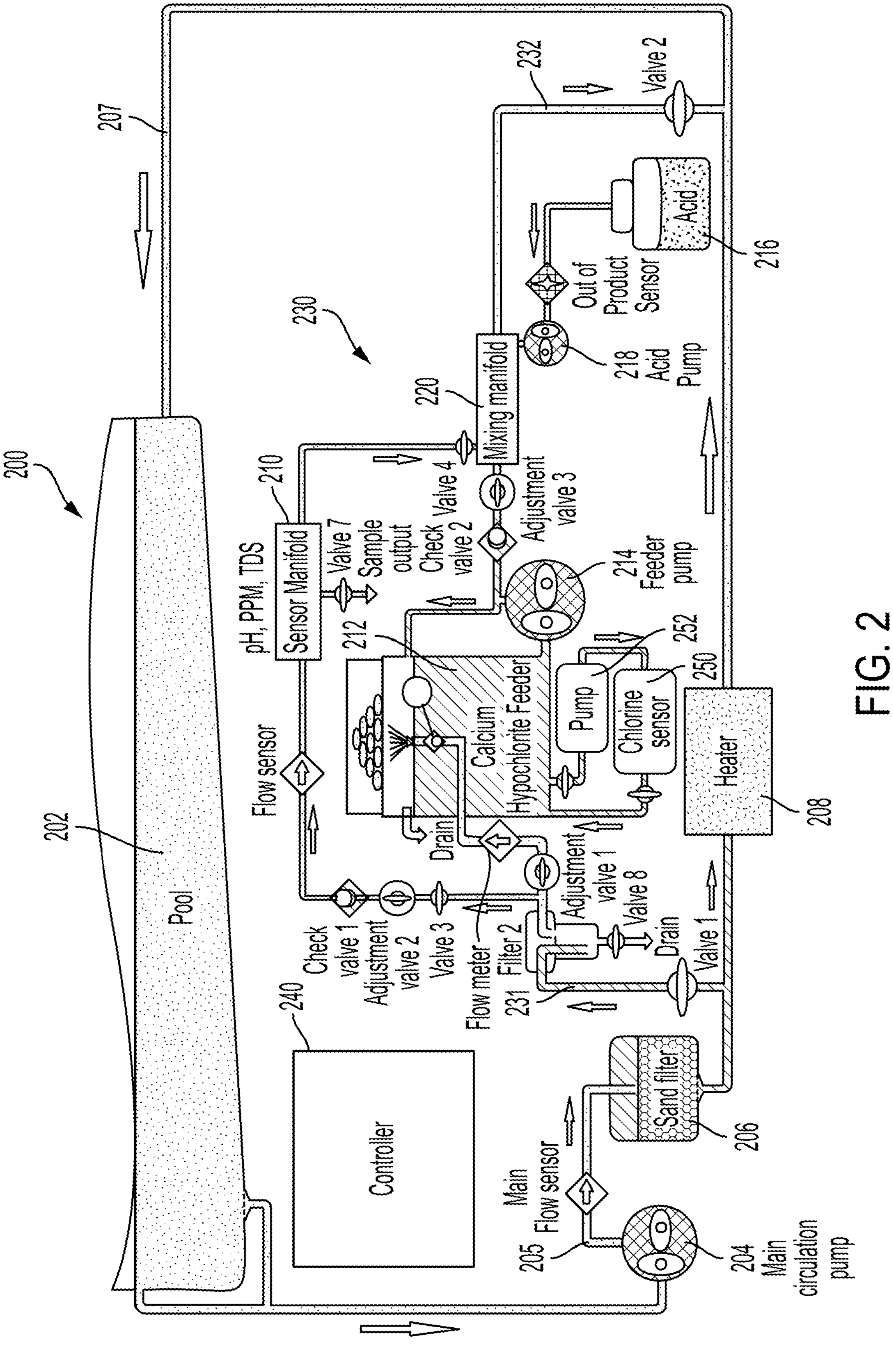
FIG. 2 is a system diagram showing components of a water monitoring and control system for maintaining water quality in a swimming pool according to some embodiments of this disclosure.

FIG. 2 is a block diagram of a system 200 for controlling water conditions in a pool volume tank or swimming pool 202. The system 200 includes a pool volume tank 202, for example a swimming pool or spa, which may hold a volume of pool water to be monitored and conditioned or treated by the system 200. System 200 includes a main circulation pump 204 for recirculating water from the pool volume tank 202 through a water recirculation loop that may include various components of system 200. For example, in the system 200 depicted in FIG. 2, main circulation pump 204 is configured to draw pool water from pool volume tank 202, move the pool water via a main flow line 205 of the recirculation loop to other components of system 200, and deliver water back to the pool volume tank 202 via a main return line 207 of the recirculation loop. In the system 200, the main flow line 205 delivers pool water drawn from pool volume tank 202 through a filter 206 to remove impurities and/or particulates and, optionally, through a heater 208 configured to raise the temperature of the pool water before returning it to the pool volume tank 202 via the return line 207.

The system 200 depicted in FIG. 2 also includes a water conditioning system 230 connected as part of the recirculation loop for monitoring and managing various aspects of pool water quality (e.g., pH, chlorine level, etc.). In the particular embodiment depicted, water conditioning system 230 is fed from the main flow line 205 via an inlet line 231, and a return line 232 delivers fluid from the conditioning system 230 to the main return line 207 for delivery back to the pool volume tank 202. The inlet line 231 is shown branching off from the main flow line 205 at a location between the filter 206 and the heater 208, although this is exemplary and the inlet line 231 could fluidly couple to other locations along the main flow line 205 in various embodiments. Water conditioning system 230 may comprise a sensor manifold 210 configured to measure a number of pool water parameters, such as pH, chlorine concentration (in ppm), temperature, total dissolved solids ("TDS") particulate concentration, etc. Water conditioning system 230 may further comprise a chlorine feeder system comprising a chlorine feeder tank 212 and a feeder pump 214. Water conditioning system 230 may also comprise an acid solution sub-system comprising an acid solution tank 216 and an acid pump 218. In embodiments, feeder pump 214 may be actuated to pump a concentrated chlorine solution from chlorine feeder tank 212 in response to a sensor of the sensor manifold 210 measuring a chlorine level of the pool water that has fallen below a predetermined threshold level, for example. In some embodiments, a controller 240 is in communication with various components and/or sensors of system 200 such that, for example, a measured chlorine concentration at sensor manifold 210 is communicated to controller 240 (e.g., via a wired or wireless communication interface, not depicted in FIG. 2), controller 240 evaluates the chlorine concentration signal or value received from sensor manifold 210, and if certain conditions are met (e.g., as determined by controller 240, for example), controller 240 may send an actuation signal to feeder pump 214 to turn on and run feeder pump 214 to begin pumping/delivering the concentrated chlorine solution from the chlorine feeder tank 212, e.g., to add the concentrated chlorine solution from the chlorine feeder tank 212 to the pool water to thereby control the chlorine concentration of the pool water in the pool volume tank 202.

Similarly, acid pump 218 may be actuated to pump an acidic solution from the acid solution tank 216 in response to a sensor of the sensor manifold 210 measuring a pH level of the pool water that has reached or crossed a predetermined threshold pH level, for example. In an analogous manner to that described above, a controller 240 may be configured to communicate with various components and/or sensors of system 200 such that a measured pH at sensor manifold 210 is communicated to controller 240 (e.g., via a wired or wireless communication interface), controller 240 evaluates the measured pH level received from sensor manifold 210, and if certain conditions are met (e.g., as determined by controller 240, for example), controller 240 may send an actuation signal to acid pump 218 to begin pumping/delivering the acidic solution from the acid solution tank 216, e.g., to add the acidic solution from acid solution tank 216 to the pool water to thereby control the pH of the pool water in the pool volume tank 202.

In some implementations, a mixing manifold 220 may be employed as part of the water conditioning system 230 as shown in FIG. 2 to facilitate mixing of pool water, concentrated chlorine solution, and/or acidic solution prior to returning the resulting solution to the pool volume tank 202 via the return line 232 and the main return line 207.

The embodiment of system 200 shown in FIG. 2 includes a feeder tank 212 comprising a calcium hypochlorite feeder tank 212, which produces and stores a concentrated chlorine solution for use with the water conditioning system 230 of system 200. In typical usage, the concentrated chlorine solution is generated by mixing calcium hypochlorite (e.g., in a powder or pellet format) with water in the feeder tank 212 to achieve a concentration of chlorine of around 200 ppm, with a typical range of about 175-225 ppm. It is noted that at this range of chlorine concentrations, the chlorine sensors that are typically used in the sensor manifold 210 to measure the concentration of chlorine in the pool volume tank 202 are not designed for measuring such high concentrations of chlorine and would most likely become saturated and/or rendered inoperable if they were exposed to such high concentrations. The chlorine sensors used in the sensor manifold 210 typically employ an electrochemical design and are intended for measuring chlorine concentrations in a range of 0-10 ppm, for example, which is more typical of the range of chlorine levels found in swimming pool water. This disclosure describes an optical sensor that may be used to measure the higher concentrations of chlorine found in a chlorine feeder tank 212 and using this information to improve the control of pool water conditions.

The system 200 of FIG. 2 includes a chlorine sensor 250 configured to measure the chlorine concentration of the concentrated chlorine solution stored in the feeder tank 212. The system 200 of FIG. 2 also includes a pump 252 that is provided to draw concentrated chlorine solution from the feeder tank 212, deliver it through chlorine sensor 250, and return the solution back into feeder tank 212. In operation, the system 200 of FIG. 2 may enable nearly continuous monitoring of the chlorine concentration in feeder tank 212 by running pump 252 and delivering the concentrated chlorine solution to the chlorine sensor 250 on a continuous (or nearly continuous, or as-needed, etc.) due in part to the fluidic isolation of chlorine sensor 250 and pump 252 from the rest of system 200. That is, the operation of other parts of the system 200, such as the main circulation pump 204, the feeder pump 214, and the acid pump 218, do not restrict the operation or use of chlorine sensor 250 in system 200.

As noted above, chlorine sensor 250 may use an optical sensing technology to enable measuring relatively high concentrations of chlorine on the order of 200 ppm. Additional details of the operation of chlorine sensor 250 are provided further below.

System 200 may enable use of information provided by chlorine sensor 250 (e.g., regarding the chlorine concentration in the feeder tank 212) into the overall management and control of pool water parameters.

It should be noted that acid pump 218 may be operated substantially independently of the above-described chlorine feeder operations, or may be operated in coordination with the chlorine feeder operations. For example, controller 240 may receive information regarding pH of the pool water, chlorine concentration of the pool water, and chlorine concentration of the chlorine feeder tank or output, and may employ a process and/or algorithm to determine whether and when to run feeder pump 214 and/or acid pump 216 to obtain the desired water quality and conditions.

Figure 3:
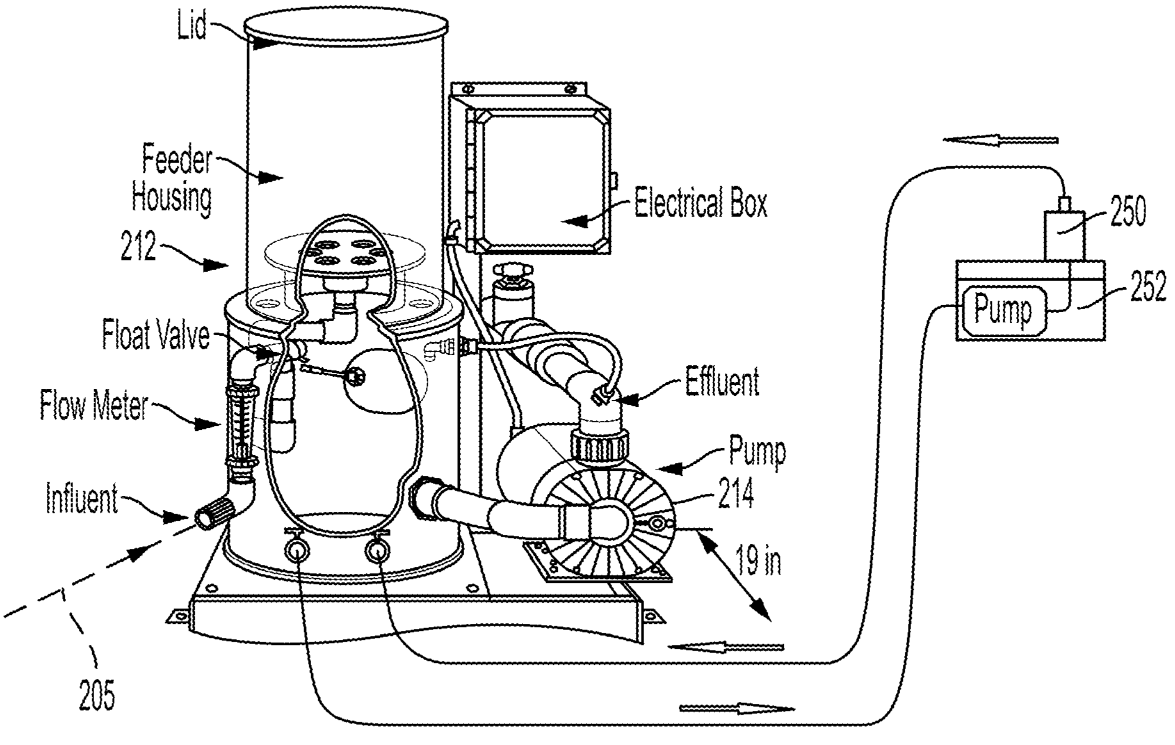
FIG. 3 is a schematic perspective view of a chlorine feeder system for monitoring and controlling aspects of water quality in a swimming pool according to some embodiments of this disclosure.

FIG. 3 is a schematic representation of a chlorine feeder portion of the system 200 of FIG. 2 (e.g., including a chlorine feeder tank 212 and a feeder pump 214), showing an exemplary arrangement for fluidically coupling chlorine sensor 250 and pump 252 to a chlorine feeder tank 212 to provide continuous and/or as-needed monitoring of chlorine concentration levels within feeder tank 212.

Option B

Option B involves connecting the chlorine sensor at the output of the feeder pump to provide flow through the chlorine sensor without the need for a dedicated pump. A flow sensor may be added in line with the chlorine sensor in such an embodiment to verify or confirm the operation of the feeder pump. In this configuration, the chlorine sensor measures the chlorine concentration at the output of the feeder pump, which may enhance the accuracy of the chlorine concentration measurement and thereby enhance the performance of the algorithm used to calculate the dispensing time (or related operating parameters) for adjusting the pool's chlorine level. The controller can also use data from the chlorine sensor to detect anomalies in the feeder operation, such as out-of-product events in the feeder tank, or malfunctioning of the feeder pump.

Figure 4:
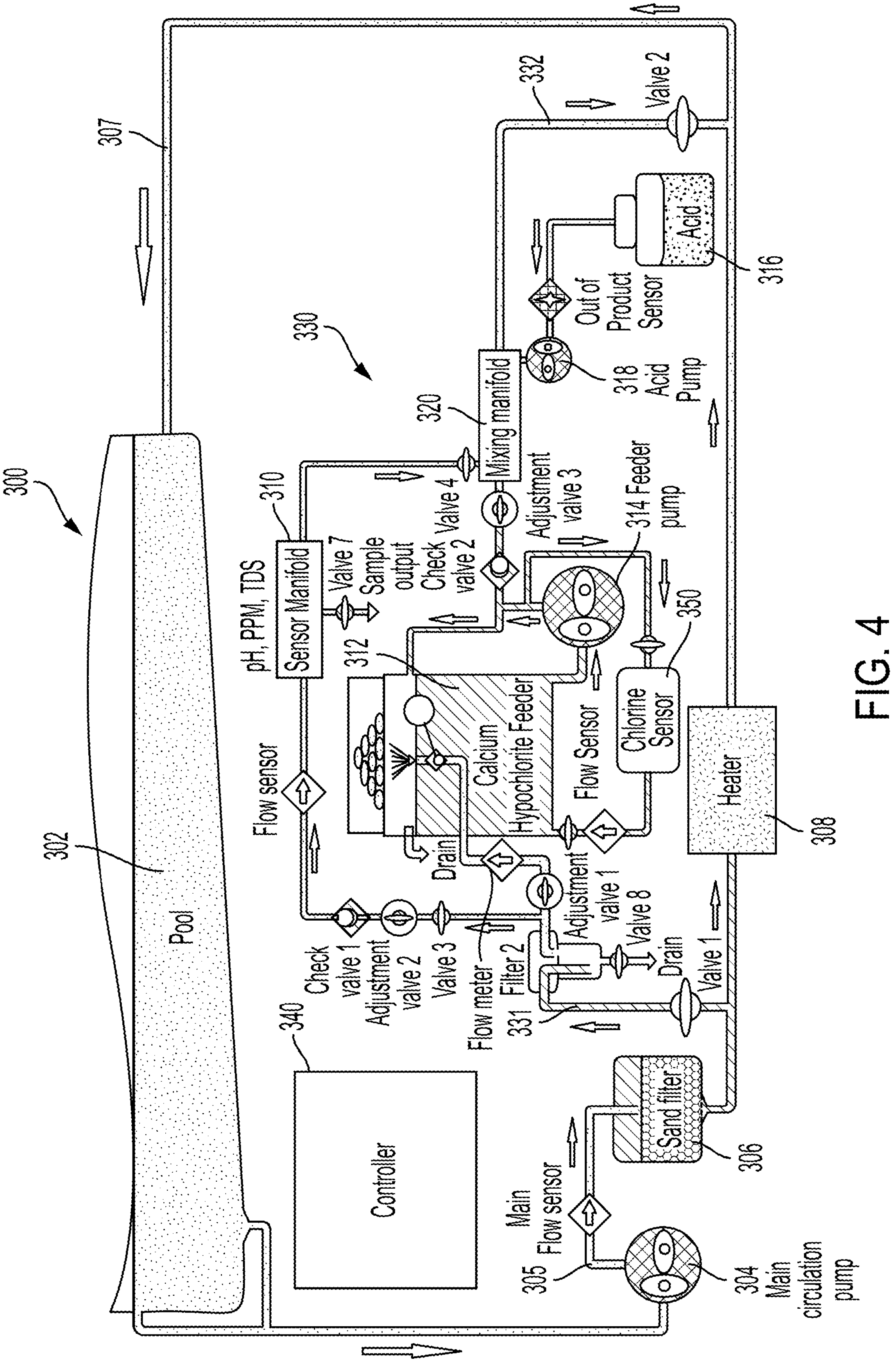
FIG. 4 is a system diagram showing components of a water monitoring and control system for maintaining water quality in a swimming pool according to some embodiments of this disclosure.

FIG. 4 is a block diagram of a system 300 for controlling water conditions in a pool volume tank or swimming pool 302. The system 300 includes a pool volume tank 302, for example a swimming pool or spa, which may hold a volume of pool water to be monitored and conditioned or treated by the system 300. System 300 includes a main circulation pump 304 for recirculating water from the pool volume tank 302 through a water recirculation loop that may include various components of system 300. For example, in the system 300 depicted in FIG. 4, main circulation pump 304 is configured to draw pool water from pool volume tank 302, deliver the pool water via a main flow line 305 to other components of system 300, and deliver water back to the pool volume tank 302 via a main return line 307. In the system 300, the main flow line 305 delivers pool water drawn from pool volume tank 302 through a filter 306 to remove impurities and/or particulates and, optionally, through a heater 308 configured to raise the temperature of the pool water before returning it to the pool volume tank 302 via the return line 307.

The system 300 depicted in FIG. 4 also includes a water conditioning system 330 connected as part of the recirculation loop for monitoring and managing various aspects of pool water quality (e.g., pH, chlorine level, etc.). In the particular embodiment depicted, conditioning system 330 is fed from the main flow line 305 via an inlet line 331, and a return line 332 delivers fluid from the conditioning system 330 to the main return line 307 for delivery back to the pool volume tank 302. The inlet line 331 is shown branching off from the main flow line 305 at a location between the filter 306 and the heater 308, although this is exemplary and the inlet line 331 could fluidly couple to other locations along the main flow line 305 in various embodiments. Water conditioning system 330 may comprise a sensor manifold 310 configured to measure a number of pool water parameters, such as pH, chlorine concentration (in ppm), temperature, total dissolved solids ("TDS") particulate concentration, etc. Water conditioning system 330 may further comprise a chlorine feeder system comprising a chlorine feeder tank 312 and a feeder pump 314. Water conditioning system 330 may also comprise an acid solution sub-system comprising an acid solution tank 316 and an acid pump 318. In embodiments, feeder pump 314 may be actuated to pump a concentrated chlorine solution from chlorine feeder tank 312 in response to a sensor of the sensor manifold 310 measuring a chlorine level of the pool water that has fallen below a predetermined threshold level, for example. In some embodiments, a controller 340 is in communication with various components and/or sensors of system 300 such that, for example, a measured chlorine concentration at sensor manifold 310 is communicated to controller 340 (e.g., via a wired or wireless communication interface, not depicted in FIG. 4), controller 340 evaluates the chlorine concentration signal or value received from sensor manifold 310, and if certain conditions are met (e.g., as determined by controller 340, for example), controller 340 may send an actuation signal to feeder pump 314 to turn on and run feeder pump 314 to begin pumping/delivering the concentrated chlorine solution from the chlorine feeder tank 312, e.g., to add the concentrated chlorine solution from the chlorine feeder tank 312 to the pool water to thereby control the chlorine concentration of the pool water in the pool volume tank 302.

Similarly, acid pump 318 may be actuated to pump an acidic solution from the acid solution tank 316 in response to a sensor of the sensor manifold 310 measuring a pH level of the pool water that has reached or crossed a predetermined threshold pH level, for example. In an analogous manner to that described above, a controller 340 may be configured to communicate with various components and/or sensors of system 300 such that a measured pH at sensor manifold 310 is communicated to controller 340 (e.g., via a wired or wireless communication interface), controller 340 evaluates the measured pH level received from sensor manifold 310, and if certain conditions are met (e.g., as determined by controller 340, for example), controller 340 may send an actuation signal to acid pump 318 to begin pumping/delivering the acidic solution from the acid solution tank 316, e.g., to add the acidic solution from acid solution tank 316 to the pool water to thereby control the pH of the pool water in the pool volume tank 302.

In some implementations, a mixing manifold 320 may be employed as part of the water conditioning system 330 as shown in FIG. 4 to facilitate mixing of pool water, concentrated chlorine solution, and/or acidic solution prior to returning the resulting solution to the pool volume tank 302 via the return line 332 and the main return line 307.

The embodiment of system 300 shown in FIG. 4 includes a feeder tank 312 comprising a calcium hypochlorite feeder tank 312, which produces and stores a concentrated chlorine solution for use with the water conditioning system 330 of system 300. In typical usage, the concentrated chlorine solution is generated by mixing calcium hypochlorite (e.g., in a powder or pellet format) with water in the feeder tank 312 to achieve a concentration of chlorine of around 200 ppm, with a typical range of about 175-225 ppm. It is noted that at this range of chlorine concentrations, the chlorine sensors that are typically used in the sensor manifold 310 to measure the concentration of chlorine in the pool volume tank 302 are not designed for measuring such high concentrations of chlorine and would most likely become saturated and/or rendered inoperable if they were exposed to such high concentrations. The chlorine sensors used in the sensor manifold 310 typically employ an electrochemical design and are intended for measuring chlorine concentrations in a range of 0-10 ppm, for example, which is more typical of the range of chlorine levels found in swimming pool water. This disclosure describes an optical sensor that may be used to measure the higher concentrations of chlorine found in a chlorine feeder tank 312 and using this information to improve the control of pool water conditions.

The system 300 of FIG. 4 includes a chlorine sensor 350 configured to measure the chlorine concentration of the concentrated chlorine solution by sampling the solution at the output of the feeder pump 314. In operation, the fluid pressure at the output of the feeder pump 314 provides the force for a portion of the fluid output to be delivered through the chlorine sensor 350 and returned to the feeder tank 312.

Chlorine sensor 350 may use an optical sensing technology to enable measuring relatively high concentrations of chlorine on the order of 200 ppm. Additional details of the operation of chlorine sensor 350 are provided further below.

System 300 may enable use of information provided by chlorine sensor 350 (e.g., regarding the chlorine concentration at the output of feeder pump 314) into the overall management and control of pool water parameters.

It should be noted that acid pump 318 may be operated substantially independently of the above-described chlorine feeder operations, or may be operated in coordination with the chlorine feeder operations. For example, controller 340 may receive information regarding pH of the pool water, chlorine concentration of the pool water, and chlorine concentration of the chlorine feeder tank or pump output, and may employ a process and/or algorithm to determine whether and when to run feeder pump 314 and/or acid pump 316 to obtain the desired water quality and conditions.

Figure 5:
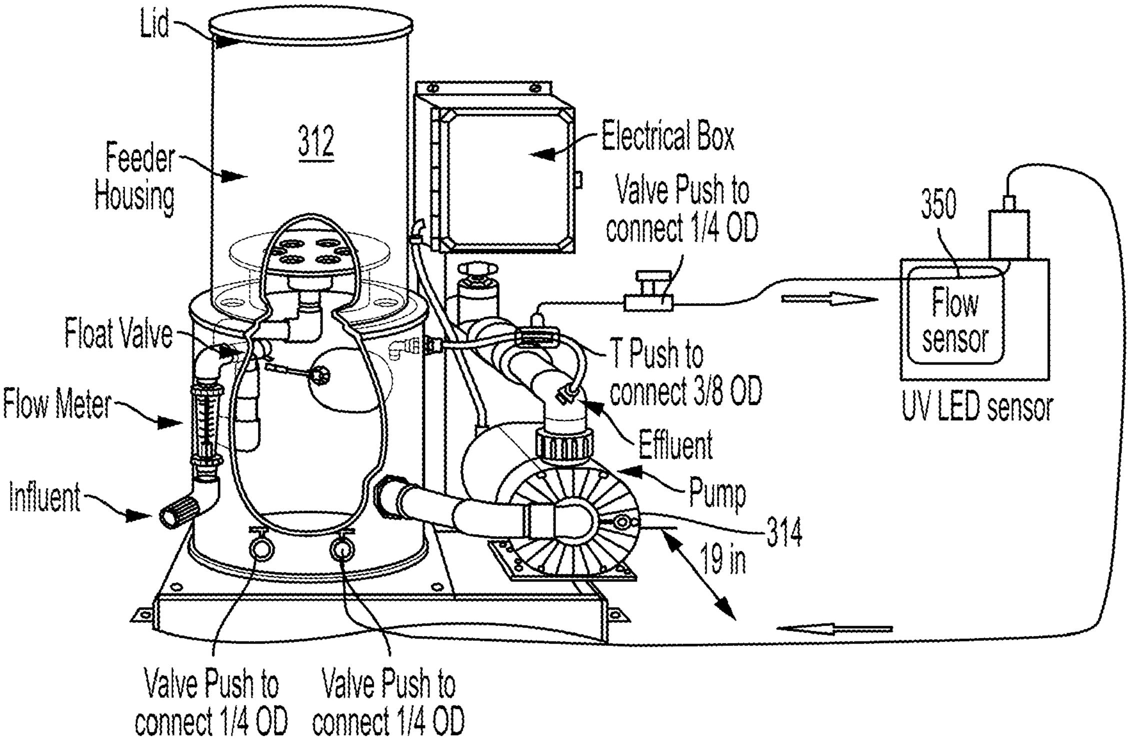
FIG. 5 is a schematic perspective view of a chlorine feeder system for monitoring and controlling aspects of water quality in a swimming pool according to some embodiments of this disclosure.

FIG. 5 is a schematic representation of a chlorine feeder portion of the system 300 of FIG. 4 (e.g., including a chlorine feeder tank 312 and a feeder pump 314), showing an exemplary arrangement for fluidically coupling chlorine sensor 350 at or near an output of feeder pump 314 to provide pressure and flow through the chlorine sensor 350 and back to the chlorine feeder tank 312.

Option C

In Option C, the chlorine sensor is selectively connected to either the output of the feeder pump or to the output of the sensor manifold via an electromechanical valve that changes position in response to changes in the operating status of the chlorine feeder pump. In this configuration, a controller activates an electromechanical valve that connects the chlorine sensor to the output of the feeder pump when the feeder pump is activated. When the electromechanical valve is activated (e.g., upon actuation of the feeder pump), the chlorine sensor measures the concentration at the feeder pump output, allowing for adjustments in the chlorine level control algorithm. When the valve is not activated (e.g., when the feeder pump is not running), the chlorine sensor is connected to the output of the sensor manifold, receiving samples from the main circulation loop. This option eliminates the need for a flow meter, as changes in chlorine readings by the chlorine sensor indicate the presence of flow and delivery of pool water samples. This configuration provides an extra level of safety protection, since the chlorine sensor can detect increased levels of chlorine in case of a failure of the PPM chlorine sensor in the sensor manifold, signaling the need for immediate correction, for example.

Figure 6:
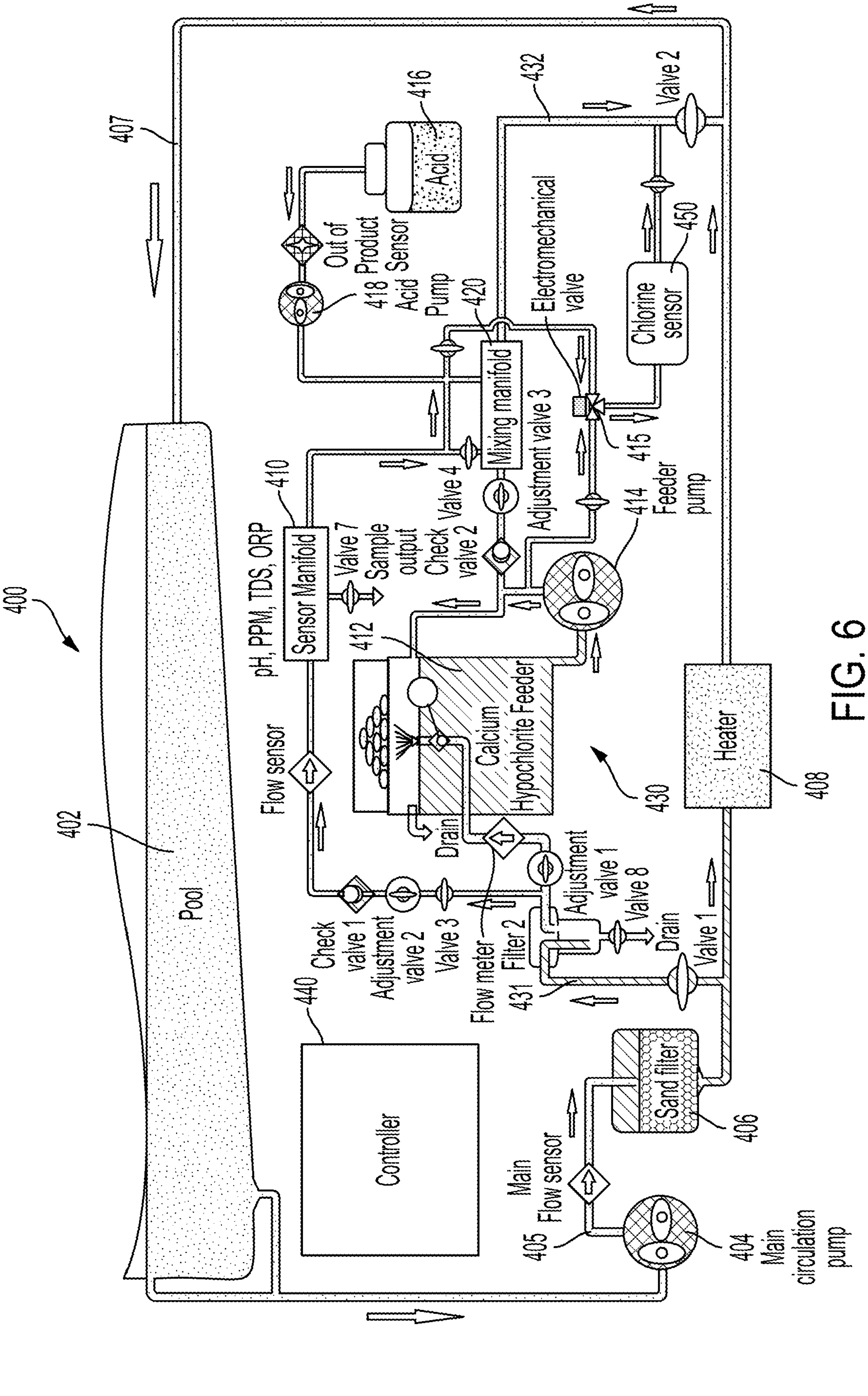
FIG. 6 is a system diagram showing components of a water monitoring and control system for maintaining water quality in a swimming pool according to some embodiments of this disclosure.

FIG. 6 is a block diagram of a system 400 for controlling water conditions in a pool volume tank or swimming pool 402. The system 400 includes a pool volume tank 402, for example a swimming pool or spa, which may hold a volume of pool water to be monitored and conditioned or treated by the system 400. System 400 includes a main circulation pump 404 for recirculating water from the pool volume tank 402 through a water recirculation loop that may include various components of system 400. For example, in the system 400 depicted in FIG. 6, main circulation pump 404 is configured to draw pool water from pool volume tank 402, deliver the pool water via a main flow line 405 to other components of system 400, and deliver water back to the pool volume tank 402 via a main return line 407. In the system 400, the main flow line 405 delivers pool water drawn from pool volume tank 402 through a filter 406 to remove impurities and/or particulates and, optionally, through a heater 408 configured to raise the temperature of the pool water before returning it to the pool volume tank 402 via the return line 407.

The system 400 depicted in FIG. 6 also includes a water conditioning system 430 connected as part of the recirculation loop for monitoring and managing various aspects of pool water quality (e.g., pH, chlorine level, etc.). In the particular embodiment depicted, conditioning system 430 is fed from the main flow line 405 via an inlet line 431, and a return line 432 delivers fluid from the conditioning system 430 to the main return line 407 for delivery back to the pool volume tank 402. The inlet line 431 is shown branching off from the main flow line 405 at a location between the filter 406 and the heater 408, although this is exemplary and the inlet line 431 could fluidly couple to other locations along the main flow line 405 in various embodiments. Water conditioning system 430 may comprise a sensor manifold 410 configured to measure a number of pool water parameters, such as pH, chlorine concentration (in ppm), temperature, total dissolved solids ("TDS") particulate concentration, etc. Water conditioning system 430 may further comprise a chlorine feeder system comprising a chlorine feeder tank 412 and a feeder pump 414. Water conditioning system 430 may also comprise an acid solution sub-system comprising an acid solution tank 416 and an acid pump 418. In embodiments, feeder pump 414 may be actuated to pump a concentrated chlorine solution from chlorine feeder tank 412 in response to a sensor of the sensor manifold 410 measuring a chlorine level of the pool water that has fallen below a predetermined threshold level, for example. In some embodiments, a controller 440 is in communication with various components and/or sensors of system 400 such that, for example, a measured chlorine concentration at sensor manifold 410 is communicated to controller 440 (e.g., via a wired or wireless communication interface, not depicted in FIG. 6), controller 440 evaluates the chlorine concentration signal or value received from sensor manifold 410, and if certain conditions are met (e.g., as determined by controller 440, for example), controller 440 may send an actuation signal to feeder pump 414 to turn on and run feeder pump 414 to begin pumping/delivering the concentrated chlorine solution from the chlorine feeder tank 412, e.g., to add the concentrated chlorine solution from the chlorine feeder tank 412 to the pool water to thereby control the chlorine concentration of the pool water in the pool volume tank 402.

Similarly, acid pump 418 may be actuated to pump an acidic solution from the acid solution tank 416 in response to a sensor of the sensor manifold 410 measuring a pH level of the pool water that has reached or crossed a predetermined threshold pH level, for example. In an analogous manner to that described above, a controller 440 may be configured to communicate with various components and/or sensors of system 400 such that a measured pH at sensor manifold 410 is communicated to controller 440 (e.g., via a wired or wireless communication interface), controller 440 evaluates the measured pH level received from sensor manifold 410, and if certain conditions are met (e.g., as determined by controller 440, for example), controller 440 may send an actuation signal to acid pump 418 to begin pumping/delivering the acidic solution from the acid solution tank 416, e.g., to add the acidic solution from acid solution tank 416 to the pool water to thereby control the pH of the pool water in the pool volume tank 402.

In some implementations, a mixing manifold 420 may be employed as part of the water conditioning system 430 as shown in FIG. 6 to facilitate mixing of pool water, concentrated chlorine solution, and/or acidic solution prior to returning the resulting solution to the pool volume tank 402 via the return line 432 and the main return line 407.

The embodiment of system 400 shown in FIG. 6 includes a feeder tank 412 comprising a calcium hypochlorite feeder tank 412, which produces and stores a concentrated chlorine solution for use with the water conditioning system 430 of system 400. In typical usage, the concentrated chlorine solution is generated by mixing calcium hypochlorite (e.g., in a powder or pellet format) with water in the feeder tank 412 to achieve a concentration of chlorine of around 200 ppm, with a typical range of about 175-225 ppm. It is noted that at this range of chlorine concentrations, the chlorine sensors that are typically used in the sensor manifold 410 to measure the concentration of chlorine in the pool volume tank 402 are not designed for measuring such high concentrations of chlorine and would most likely become saturated and/or rendered inoperable if they were exposed to such high concentrations. The chlorine sensors used in the sensor manifold 410 typically employ an electrochemical design and are intended for measuring chlorine concentrations in a range of 0-10 ppm, for example, which is more typical of the range of chlorine levels found in swimming pool water. This disclosure describes an optical sensor that may be used to measure the higher concentrations of chlorine found in a chlorine feeder tank 412 and using this information to improve the control of pool water conditions.

The system 400 of FIG. 6 includes a chlorine sensor 450 that is selectively fluidly coupled to the output of the feeder pump 414 via an electromechanical valve 415. The electromechanical valve 415 has two fluid coupling positions determined by the status of the feeder pump 414 being either off or on. When the feeder pump 414 is on, the electromechanical valve 415 assumes a first position that directs fluid from the feeder pump 414 output through the chlorine sensor 450. When the feeder pump 414 is off, the electromechanical valve 415 assumes a second position that directs fluid from the sensor manifold 410 to the chlorine sensor 450.

System 400 may eliminate the need for a flow meter, since changes in chlorine levels measured by chlorine sensor 450 indicate the presence of flow. This configuration can thereby provide an extra layer of safety, since chlorine sensor 450 may be able to detect increased levels of chlorine in the pool water in case of a failure of the PPM chlorine sensor in the sensor manifold 410, which could trigger an alarm and/or signal the need for immediate action or correction, for example.

Chlorine sensor 450 may use an optical sensing technology to enable measuring relatively high concentrations of chlorine on the order of 200 ppm. Additional details of the operation of chlorine sensor 450 are provided further below.

System 400 may enable use of information provided by chlorine sensor 450 (e.g., regarding the chlorine concentration at the output of feeder pump 414) into the overall management and control of pool water parameters.

It should be noted that acid pump 418 may be operated substantially independently of the above-described chlorine feeder operations, or may be operated in coordination with the chlorine feeder operations. For example, controller 440 may receive information regarding pH of the pool water, chlorine concentration of the pool water, and chlorine concentration of the chlorine feeder tank or pump output, and may employ a process and/or algorithm to determine whether and when to run feeder pump 414 and/or acid pump 416 to obtain the desired water quality and conditions.

Option D

Option D involves connecting the chlorine sensor to the mixing manifold. The output of the chlorine sensor is connected to a point in the return line where the solution from the feeder and water from the sensor manifold are directed back into the main circulation loop. When the chlorine feeder pump is activated in this configuration, the concentrated chlorine solution from the feeder tank flows through the chlorine sensor, and when the feeder pump is stopped, the pool water passing through from the sensor manifold flows through the chlorine sensor. An optional adjustment valve may be positioned between the mixing manifold and the connection point in the return line to create a small pressure difference and increase flow through the chlorine sensor as needed. Alternatively, the chlorine sensor may be installed directly in-line with the return line, with all flow from the mixing manifold passing through the chlorine sensor and returning to the main circulation loop.

Figure 7A:
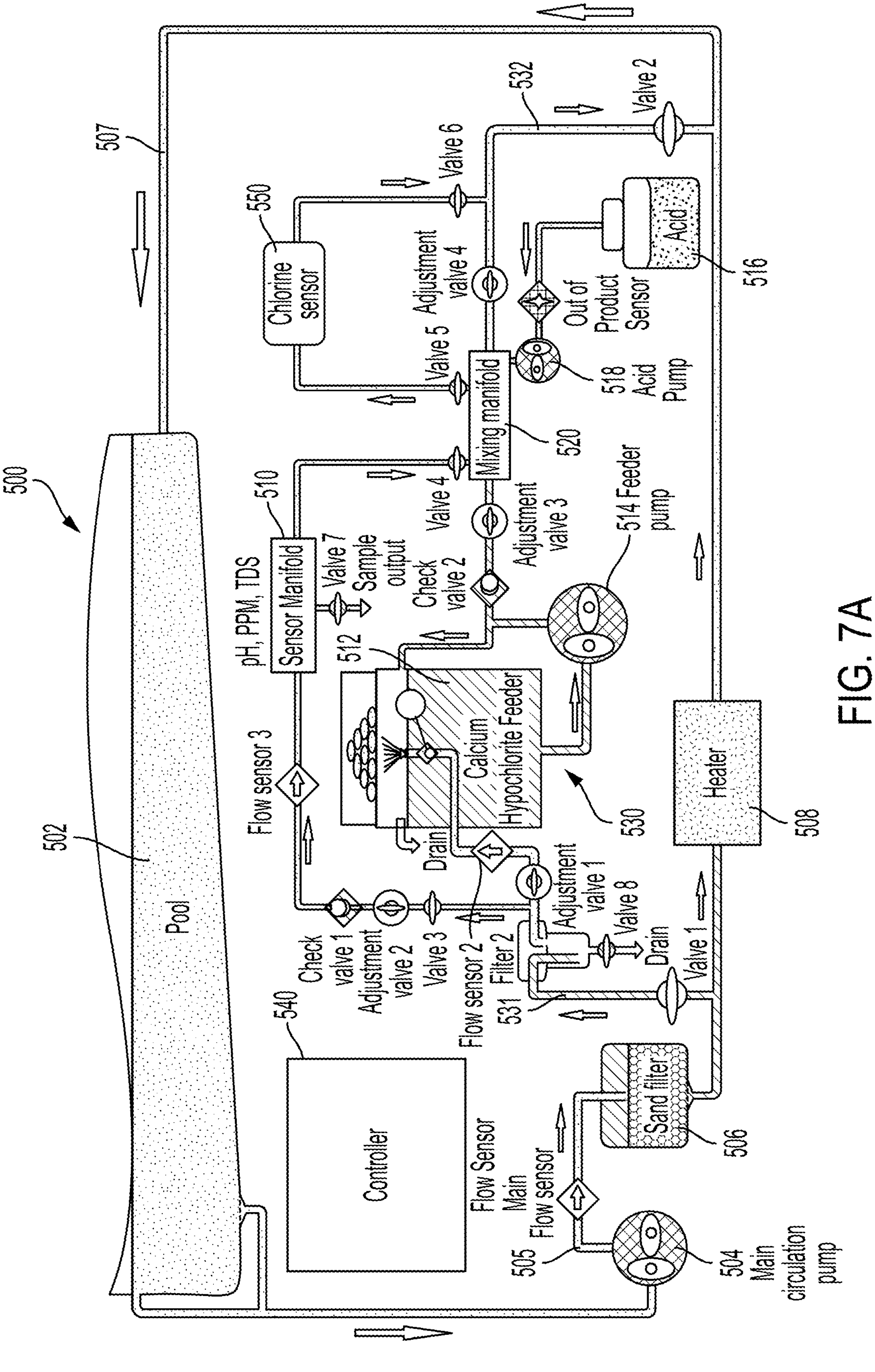
FIG. 7A is a system diagram showing components of a water monitoring and control system for maintaining water quality in a swimming pool according to some embodiments of this disclosure.

FIG. 7A is a block diagram of a system 500 for controlling water conditions in a pool volume tank or swimming pool 502. The system 500 includes a pool volume tank 502, for example a swimming pool or spa, which may hold a volume of pool water to be monitored and conditioned or treated by the system 500. System 500 includes a main circulation pump 504 for recirculating water from the pool volume tank 502 through a water recirculation loop that may include various components of system 500. For example, in the system 500 depicted in FIG. 7A, main circulation pump 504 is configured to draw pool water from pool volume tank 502, deliver the pool water via a main flow line 505 to other components of system 500, and deliver water back to the pool volume tank 502 via a main return line 507. In the system 500, the main flow line 505 delivers pool water drawn from pool volume tank 502 through a filter 506 to remove impurities and/or particulates and, optionally, through a heater 508 configured to raise the temperature of the pool water before returning it to the pool volume tank 502 via the return line 407.

The system 500 depicted in FIG. 7A also includes a water conditioning system 530 connected as part of the recirculation loop for monitoring and managing various aspects of pool water quality (e.g., pH, chlorine level, etc.). In the particular embodiment depicted, conditioning system 530 is fed from the main flow line 505 via an inlet line 531, and a return line 532 delivers fluid from the conditioning system 530 to the main return line 507 for delivery back to the pool volume tank 502. The inlet line 531 is shown branching off from the main flow line 505 at a location between the filter 506 and the heater 508, although this is exemplary and the inlet line 531 could fluidly couple to other locations along the main flow line 505 in various embodiments. Water conditioning system 530 may comprise a sensor manifold 510 configured to measure a number of pool water parameters, such as pH, chlorine concentration (in ppm), temperature, total dissolved solids ("TDS") particulate concentration, etc. Water conditioning system 530 may further comprise a chlorine feeder system comprising a chlorine feeder tank 512 and a feeder pump 514. Water conditioning system 530 may also comprise an acid solution sub-system comprising an acid solution tank 516 and an acid pump 518. In embodiments, feeder pump 514 may be actuated to pump a concentrated chlorine solution from chlorine feeder tank 512 in response to a sensor of the sensor manifold 510 measuring a chlorine level of the pool water that has fallen below a predetermined threshold level, for example. In some embodiments, a controller 540 is in communication with various components and/or sensors of system 500 such that, for example, a measured chlorine concentration at sensor manifold 510 is communicated to controller 540 (e.g., via a wired or wireless communication interface, not depicted in FIG. 7A), controller 540 evaluates the chlorine concentration signal or value received from sensor manifold 510, and if certain conditions are met (e.g., as determined by controller 540, for example), controller 540 may send an actuation signal to feeder pump 514 to turn on and run feeder pump 514 to begin pumping/delivering the concentrated chlorine solution from the chlorine feeder tank 512, e.g., to add the concentrated chlorine solution from the chlorine feeder tank 512 to the pool water to thereby control the chlorine concentration of the pool water in the pool volume tank 502.

Similarly, acid pump 518 may be actuated to pump an acidic solution from the acid solution tank 516 in response to a sensor of the sensor manifold 510 measuring a pH level of the pool water that has reached or crossed a predetermined threshold pH level, for example. In an analogous manner to that described above, a controller 540 may be configured to communicate with various components and/or sensors of system 500 such that a measured pH at sensor manifold 510 is communicated to controller 540 (e.g., via a wired or wireless communication interface), controller 540 evaluates the measured pH level received from sensor manifold 510, and if certain conditions are met (e.g., as determined by controller 540, for example), controller 540 may send an actuation signal to acid pump 518 to begin pumping/delivering the acidic solution from the acid solution tank 516, e.g., to add the acidic solution from acid solution tank 516 to the pool water to thereby control the pH of the pool water in the pool volume tank 502.

In some implementations, a mixing manifold 520 may be employed as part of the water conditioning system 530 as shown in FIG. 7A to facilitate mixing of pool water, concentrated chlorine solution, and/or acidic solution prior to returning the resulting solution to the pool volume tank 502 via the return line 532 and the main return line 507.

The embodiment of system 500 shown in FIG. 7A includes a feeder tank 512 comprising a calcium hypochlorite feeder tank 512, which produces and stores a concentrated chlorine solution for use with the water conditioning system 530 of system 500. In typical usage, the concentrated chlorine solution is generated by mixing calcium hypochlorite (e.g., in a powder or pellet format) with water in the feeder tank 512 to achieve a concentration of chlorine of around 200 ppm, with a typical range of about 175-225 ppm. It is noted that at this range of chlorine concentrations, the chlorine sensors that are typically used in the sensor manifold 510 to measure the concentration of chlorine in the pool volume tank 502 are not designed for measuring such high concentrations of chlorine and would most likely become saturated and/or rendered inoperable if they were exposed to such high concentrations. The chlorine sensors used in the sensor manifold 510 typically employ an electrochemical design and are intended for measuring chlorine concentrations in a range of 0-10 ppm, for example, which is more typical of the range of chlorine levels found in swimming pool water. This disclosure describes an optical sensor that may be used to measure the higher concentrations of chlorine found in a chlorine feeder tank 512 and using this information to improve the control of pool water conditions.

The system 500 of FIG. 7A includes a chlorine sensor 550 that is fluidly coupled to the mixing manifold 520. The output of the chlorine sensor 550 is connected to a point in the return line 532 where the solution from the feeder and water from the sensor manifold are directed back into the main return line 507 of the main circulation loop. When the chlorine feeder pump 514 is activated and running in this configuration, the concentrated chlorine solution from the feeder tank 512 flows through the chlorine sensor 550, and when the feeder pump 514 is not running, the pool water passing through from the sensor manifold 510 flows through the chlorine sensor 550. An optional adjustment valve may be positioned between the mixing manifold 520 and the connection point in the return line 532 to create a pressure difference and thereby increase flow through the chlorine sensor 550 as needed. Alternatively, the chlorine sensor 550 may be installed directly in-line with the return line 532, such that all flow from the mixing manifold 520 passes through the chlorine sensor 550 and returns to the main return line 507 and to the pool volume tank 502.

Figure 7B:
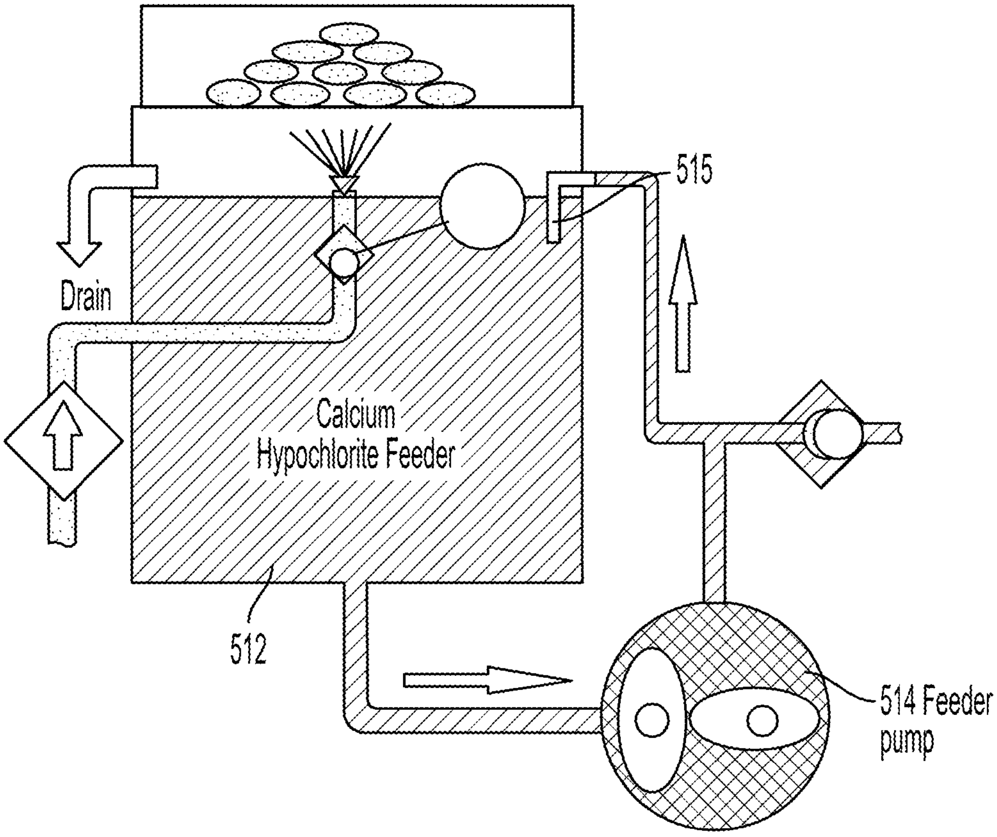
FIG. 7B is an enlarged portion of the system diagram of FIG. 7A showing aspects of a chlorine feeder system for a swimming pool according to some embodiments of this disclosure.

FIG. 7B illustrates an aspect of an exemplary chlorine feeder system that may be applicable to various embodiments; it is shown with reference to the system 500 of FIG. 7A, but it could apply as well to the system embodiments depicted in any of FIGS. 2, 4, 6 and 8. As shown in FIG. 7B, the chlorine feeder system may comprise a chlorine feeder tank 512 and a feeder pump 514 arranged such that a portion of the output of the feeder pump 514, when running, is directed back to the chlorine feeder tank 512 via a return line (e.g., to thereby cause mixing of the concentrated chlorine solution therein). In some embodiments, it may be desirable to have the return line enter the chlorine feeder tank 512 at a position (e.g., at a height of the tank 512) that is above the level of the chlorine solution in the feeder tank 512. It may also be desirable to have a length of internal tubing 515 that directs the flow from the return line into tank 512 to a level that is immersed in the chlorine solution, as shown generally in FIG. 7B. This may, for example, provide a desired vortex for mixing the chlorine solution, while helping avoid the formation of foam and bubbles in the solution, which could affect the ability of the chlorine sensor 550 to provide accurate readings.

Chlorine sensor 550 may use an optical sensing technology to enable measuring relatively high concentrations of chlorine on the order of 200 ppm. Additional details of the operation of chlorine sensor 550 are provided further below.

System 500 may enable use of information provided by chlorine sensor 550 (e.g., regarding the chlorine concentration at the output of feeder pump 514) into the overall management and control of pool water parameters.

It should be noted that acid pump 518 may be operated substantially independently of the above-described chlorine feeder operations, or may be operated in coordination with the chlorine feeder operations. For example, controller 540 may receive information regarding pH of the pool water, chlorine concentration of the pool water, and chlorine concentration of the chlorine feeder tank or pump output, and may employ a process and/or algorithm to determine whether and when to run feeder pump 514 and/or acid pump 516 to obtain the desired water quality and conditions.

Option E

In Option E, the chlorine sensor is connected to a location within the water conditioning system that is convenient for connection and disconnection and use.

Figure 8:
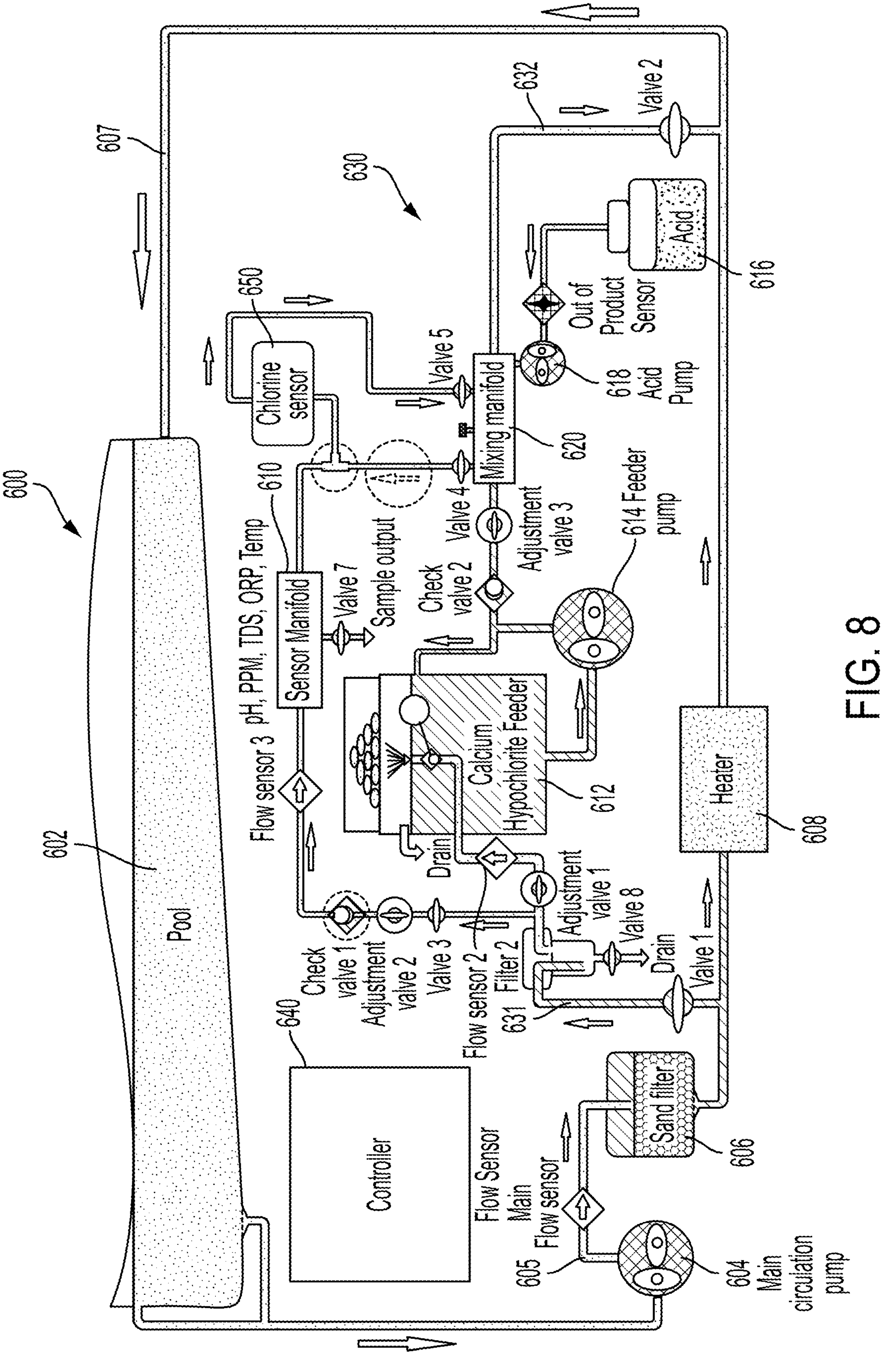
FIG. 8 is a system diagram showing components of a water monitoring and control system for maintaining water quality in a swimming pool according to some embodiments of this disclosure.

FIG. 8 is a block diagram of a system 600 for controlling water conditions in a pool volume tank or swimming pool 602. The system 600 includes a pool volume tank 602, for example a swimming pool or spa, which may hold a volume of pool water to be monitored and conditioned or treated by the system 600. System 600 includes a main circulation pump 604 for recirculating water from the pool volume tank 602 through a water recirculation loop that may include various components of system 600. For example, in the system 600 depicted in FIG. 8, main circulation pump 604 is configured to draw pool water from pool volume tank 602, deliver the pool water via a main flow line 605 to other components of system 600, and deliver water back to the pool volume tank 602 via a main return line 607. In the system 600, the main flow line 605 delivers pool water drawn from pool volume tank 602 through a filter 606 to remove impurities and/or particulates and, optionally, through a heater 608 configured to raise the temperature of the pool water before returning it to the pool volume tank 602 via the return line 607.

The system 600 depicted in FIG. 8 also includes a water conditioning system 630 connected as part of the recirculation loop for monitoring and managing various aspects of pool water quality (e.g., pH, chlorine level, etc.). In the particular embodiment depicted, conditioning system 630 is fed from the main flow line 605 via an inlet line 631, and a return line 632 delivers fluid from the conditioning system 630 to the main return line 607 for delivery back to the pool volume tank 602. The inlet line 631 is shown branching off from the main flow line 605 at a location between the filter 606 and the heater 608, although this is exemplary and the inlet line 631 could fluidly couple to other locations along the main flow line 605 in various embodiments. Water conditioning system 630 may comprise a sensor manifold 610 configured to measure a number of pool water parameters, such as pH, chlorine concentration (in ppm), temperature, total dissolved solids ("TDS") particulate concentration, etc. Water conditioning system 630 may further comprise a chlorine feeder system comprising a chlorine feeder tank 612 and a feeder pump 614. Water conditioning system 630 may also comprise an acid solution sub-system comprising an acid solution tank 616 and an acid pump 618. In embodiments, feeder pump 614 may be actuated to pump a concentrated chlorine solution from chlorine feeder tank 612 in response to a sensor of the sensor manifold 610 measuring a chlorine level of the pool water that has fallen below a predetermined threshold level, for example. In some embodiments, a controller 640 is in communication with various components and/or sensors of system 600 such that, for example, a measured chlorine concentration at sensor manifold 610 is communicated to controller 640 (e.g., via a wired or wireless communication interface, not depicted in FIG. 8), controller 640 evaluates the chlorine concentration signal or value received from sensor manifold 610, and if certain conditions are met (e.g., as determined by controller 640, for example), controller 640 may send an actuation signal to feeder pump 614 to turn on and run feeder pump 614 to begin pumping/delivering the concentrated chlorine solution from the chlorine feeder tank 612, e.g., to add the concentrated chlorine solution from the chlorine feeder tank 612 to the pool water to thereby control the chlorine concentration of the pool water in the pool volume tank 602.

Similarly, acid pump 618 may be actuated to pump an acidic solution from the acid solution tank 616 in response to a sensor of the sensor manifold 610 measuring a pH level of the pool water that has reached or crossed a predetermined threshold pH level, for example. In an analogous manner to that described above, a controller 640 may be configured to communicate with various components and/or sensors of system 600 such that a measured pH at sensor manifold 610 is communicated to controller 640 (e.g., via a wired or wireless communication interface), controller 640 evaluates the measured pH level received from sensor manifold 610, and if certain conditions are met (e.g., as determined by controller 640, for example), controller 640 may send an actuation signal to acid pump 618 to begin pumping/delivering the acidic solution from the acid solution tank 616, e.g., to add the acidic solution from acid solution tank 616 to the pool water to thereby control the pH of the pool water in the pool volume tank 602.

In some implementations, a mixing manifold 620 may be employed as part of the water conditioning system 630 as shown in FIG. 8 to facilitate mixing of pool water, concentrated chlorine solution, and/or acidic solution prior to returning the resulting solution to the pool volume tank 602 via the return line 632 and the main return line 607.

The embodiment of system 600 shown in FIG. 8 includes a feeder tank 612 comprising a calcium hypochlorite feeder tank 612, which produces and stores a concentrated chlorine solution for use with the water conditioning system 630 of system 600. In typical usage, the concentrated chlorine solution is generated by mixing calcium hypochlorite (e.g., in a powder or pellet format) with water in the feeder tank 612 to achieve a concentration of chlorine of around 200 ppm, with a typical range of about 175-225 ppm. It is noted that at this range of chlorine concentrations, the chlorine sensors that are typically used in the sensor manifold 610 to measure the concentration of chlorine in the pool volume tank 602 are not designed for measuring such high concentrations of chlorine and would most likely become saturated and/or rendered inoperable if they were exposed to such high concentrations. The chlorine sensors used in the sensor manifold 610 typically employ an electrochemical design and are intended for measuring chlorine concentrations in a range of 0-10 ppm, for example, which is more typical of the range of chlorine levels found in swimming pool water. This disclosure describes an optical sensor that may be used to measure the higher concentrations of chlorine found in a chlorine feeder tank 612 and using this information to improve the control of pool water conditions.

The system 600 of FIG. 8 includes a chlorine sensor 650 configured to measure the chlorine concentration of the concentrated chlorine solution stored in the feeder tank 612, or at some point downstream of feeder pump 614. As noted above, chlorine sensor 650 may use an optical sensing technology to enable measuring relatively high concentrations of chlorine on the order of 200 ppm. Additional details of the operation of chlorine sensor 650 are provided further below.

In operation, the system 600 of FIG. 8 may be configured, for example, as a result of connecting chlorine sensor 650 to an existing pool water conditioning system substantially as shown in FIG. 8. Thus, system 600 may provide a convenient or simple method of incorporating chlorine sensor 650 into existing pool water maintenance operations due to the relatively simple connections involved, and/or it may provide convenience in operation and use. System 600 may also enable use of information provided by chlorine sensor 650 (e.g., regarding the chlorine concentration in the feeder tank 612) into the overall management and control of pool water parameters. As shown, chlorine sensor 650 is connected in parallel with the mixing manifold 620.

When the feeder pump 614 is not running, the flow of pool water into the water conditioning system via inlet line 631 flows through the sensor manifold 610, then branches off and flows through both the chlorine sensor 650 and the mixing manifold 620 before rejoining in the return line 632. During such operations, chlorine sensor 650 may act as a back-up sensor to the chlorine sensor of the sensor manifold 610 and may also be used to confirm flow through the water conditioning system 630.

When the feeder pump 614 is running, the higher pressure at the output of the feeder pump 614 will prevent the flow of pool water through the sensor manifold 610 (due to the action of a check valve disposed in-line with the sensor manifold 610), and concentrated chlorine solution from the feeder tank 612 will flow through both the chlorine sensor 650 and the mixing manifold 620 before rejoining in the return line 632. During such operations, chlorine sensor 650 is receiving fluid flow from the output of the feeder pump and can therefore measure the concentration of the concentrated chlorine solution.

It should be noted that acid pump 618 may be operated substantially independently of the above-described chlorine feeder operations, or may be operated in coordination with the chlorine feeder operations. For example, controller 640 may receive information regarding pH of the pool water, chlorine concentration of the pool water, and chlorine concentration of the chlorine feeder tank or output, and may employ a process and/or algorithm to determine whether and when to run feeder pump 614 and/or acid pump 616 to obtain the desired water quality and conditions.

The exemplary options described above provide various configurations for monitoring the concentrated chlorine solution associated with a chlorine feeder system of a pool fluidic system, which may thereby allow for more precise control and adjustments to maintain the desired chlorine level in the pool water of the pool volume tank. The selection of an appropriate option from those described above may depend on a number of factors including, for example, existing system design, accuracy requirements, safety considerations, cost, and convenience, among other considerations.

Method and Device for Monitoring Chlorine Concentration Associated with Calcium Hypochlorite Feeder System As discussed hereinabove, a chlorine feeder system (e.g., a calcium hypochlorite feeder system) may be employed to dispense a concentrated chlorine solution into the pool water recirculation loop in order to maintain the chlorine level of the pool water in a pool volume tank within a desired range of chlorine concentrations.

A calcium hypochlorite feeder system in accordance with this disclosure may include a chlorine feeder tank for producing and storing a concentrated chlorine solution, and a feeder pump having an input line connected to the feeder tank and an output line to deliver the concentrated chlorine solution to the main recirculation loop. In some embodiments, a portion of the output flow from the feeder pump may be returned to the feeder tank to create a vortex, which may improve mixing during operation. In some implementations, such as that described above with reference to FIG. 7B, the return line from the output of the feeder pump to the feeder tank may be immersed in the concentrated chlorine solution to reduce the formation of bubbles; the immersion may occur internal to the feeder tank, e.g., via internal tubing, for example. Additional aspects of the chlorine feeder system may include an input line with a valve (e.g., a shut-off float valve), and a container holding calcium hypochlorite tablets for producing the concentrated chlorine solution in the feeder tank. The shut-off float valve, for example, may be used to maintain a certain desired level of fluid in the feeder tank according to some embodiments. Calcium hypochlorite tablets in the container may, for example, be stored dry and/or only partially immersed in water. In some embodiments, the calcium hypochlorite tablets move from a relatively dry area into a lower level (and thereby immersed in liquid) as the tablets towards the bottom portion of the container are dissolved. The feeder dimensions, volume, and flow rate are designed to produce, in normal operations, a concentrated chlorine solution having a chlorine concentration near 200 ppm.

The pH level corresponding to a 200 ppm chlorine solution is typically above a pH of 9, and this property creates a favorable condition for measuring chlorine concentration using a UV absorbance sensor. For example, a UV absorbance sensor according to this disclosure may function reasonably well to measure chlorine concentration in a fluid having a pH in a range of about 8.5 to about 12.0, and preferably a pH in a range of about 10.0 to 11.0, according to some embodiments.

Figure 17B:
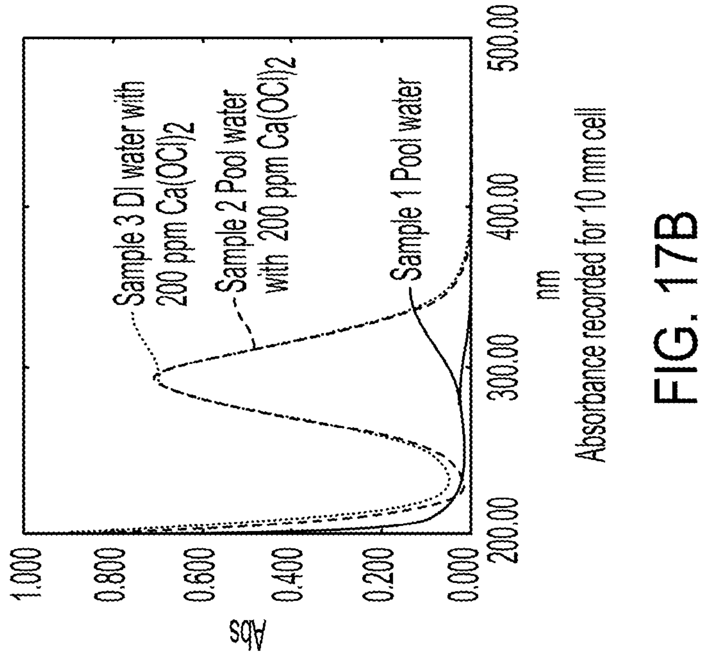
FIG. 17A thru 17D are plots showing absorbance of light energy as a function of wavelength for the UV chlorine sensor system according to some embodiments of this disclosure.
Figure 17A:
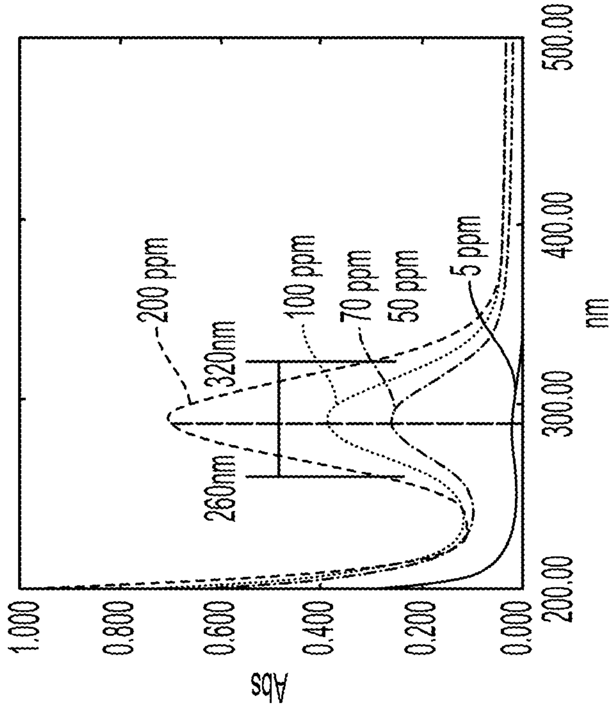

FIG. 17A shows plots of UV absorbance as a function of light wavelength (in nanometers or nm) measured for a number of calcium hypochlorite solutions having different concentrations (e.g., 5 ppm, 50 ppm, 70 ppm, 100 ppm, and 200 ppm). It was observed (as shown in FIG. 17A) that light having a wavelength in a range of about 260 nm to 320 nm (and preferably around 290 nm) can be used to estimate the chlorine concentration (e.g., from a chlorine concentration of about 5 ppm to 200 ppm). For each of the varying chlorine concentrations in the fluid samples, the plot of light absorbance in FIG. 17A showed a peak value centered at approximately 290 nm, and the relative magnitude of the measured light absorbance was roughly proportional to the chlorine concentration in each instance.

Figure 17C:
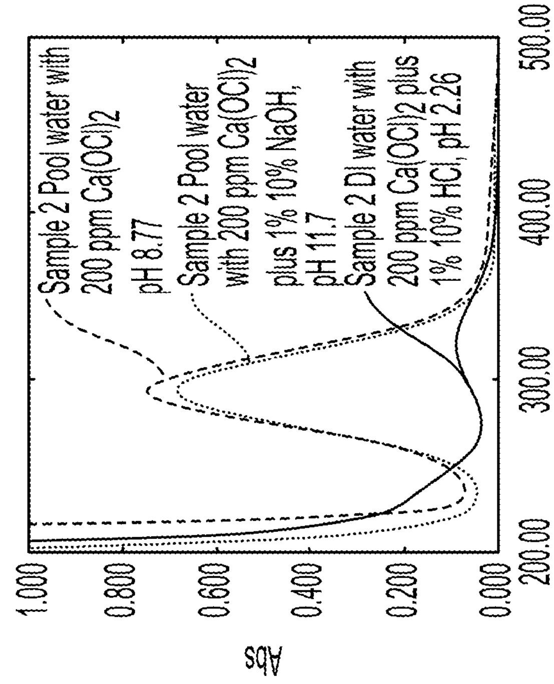
Figure 17D:
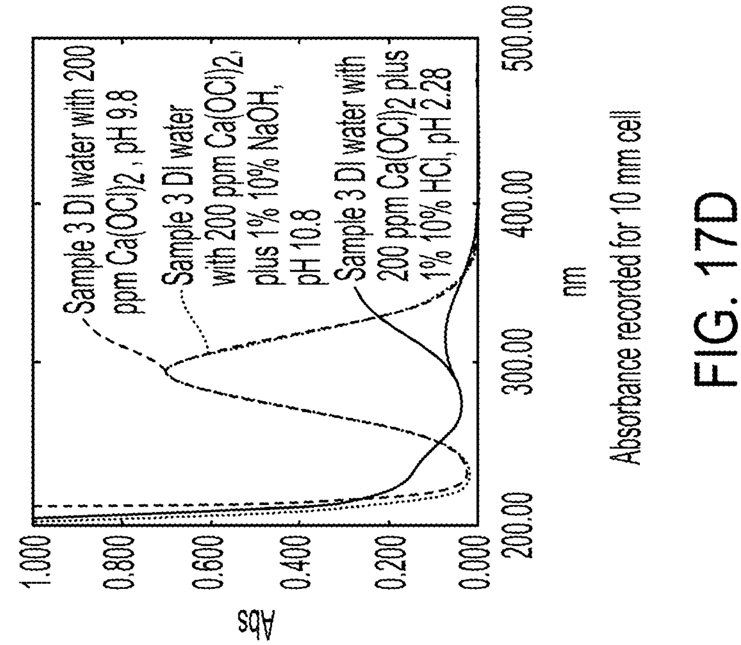

FIGS. 17B-17D show additional plots of light absorbance data that help to validate the use of a UV absorbance sensor for measuring chlorine concentration, particularly when used to measure fluids having relatively high concentrations of chlorine, and when the fluids have a pH value in a certain range. For example, in FIG. 17B, samples 2 and 3 show nearly identical plots of absorbance with a "spike" near 290 nm for 2 different solutions having 200 ppm calcium hypochlorite, despite sample 2 being a concentrated chlorinated pool water and sample 3 being de-ionized (DI) water. The sample 1 plot in FIG. 17B for light absorbance of "normal" pool water (e.g., having an estimated chlorine concentration of ~4 ppm) is much different and does not have a large, distinct spike near a wavelength of 290 nm. FIGS. 17C and 17D show that the UV absorbance sensor works reasonably well to estimate chlorine concentration around a value of about 200 ppm when the pH of the fluid sample is within a pH range of 8.77 to 11.7 (see FIG. 17C), and works very well when the pH of the fluid sample is within a pH range of 9.8 to 10.8 (see FIG. 17D). As shown, the results plotted for fluids having pH values of 2.26 and 2.28 in FIGS. 17C and 17D, respectively, do not correlate well, either in amplitude or in peak frequency, for example.

Based on the results observed in FIGS. 17A-17D, a UV absorbance sensor was proposed as a sensor for measuring chlorine concentration of the chlorine feeder system, since the expected values of chlorine concentrations and PH levels associated with the chlorine feeder system both fall well within the ranges in which the UV absorbance sensor of this disclosure were demonstrated to function well to estimate chlorine concentration.

It is also noted that UV spectrometers configured to detect light energy in such short wavelength ranges tend to be quite expensive. However, by using UV LEDs as light sources and sapphire ball lenses as exemplary materials for an optical cell, a low-cost, UV absorbance chlorine sensor could be produced to detect and measure the chlorine concentration of the concentrated chlorine solution of the chlorine feeder tank of a pool system.

The proposed device comprises a chlorine sensor, an optical cell, and a control system. The chlorine sensor utilizes UV LEDs as light sources configured to emit light having a wavelength within the range of 260 nm to 320 nm, which is suitable for chlorine concentration measurement.

The optical cell, made of sapphire ball lenses, allows the UV light energy emitted by the UV LEDs to pass through the chlorine solution and thereby detect the UV absorbance. The control system provides data acquisition and analysis functions of the device. The control system of the device may include a microcontroller or similar device to receive signals from the chlorine sensor and to process the UV absorbance data. The microcontroller may also be connected to a display unit or interface for real-time monitoring of the chlorine concentration. The microcontroller can also be connected to a data logging system for recording and analyzing historical data.

Figure 18:
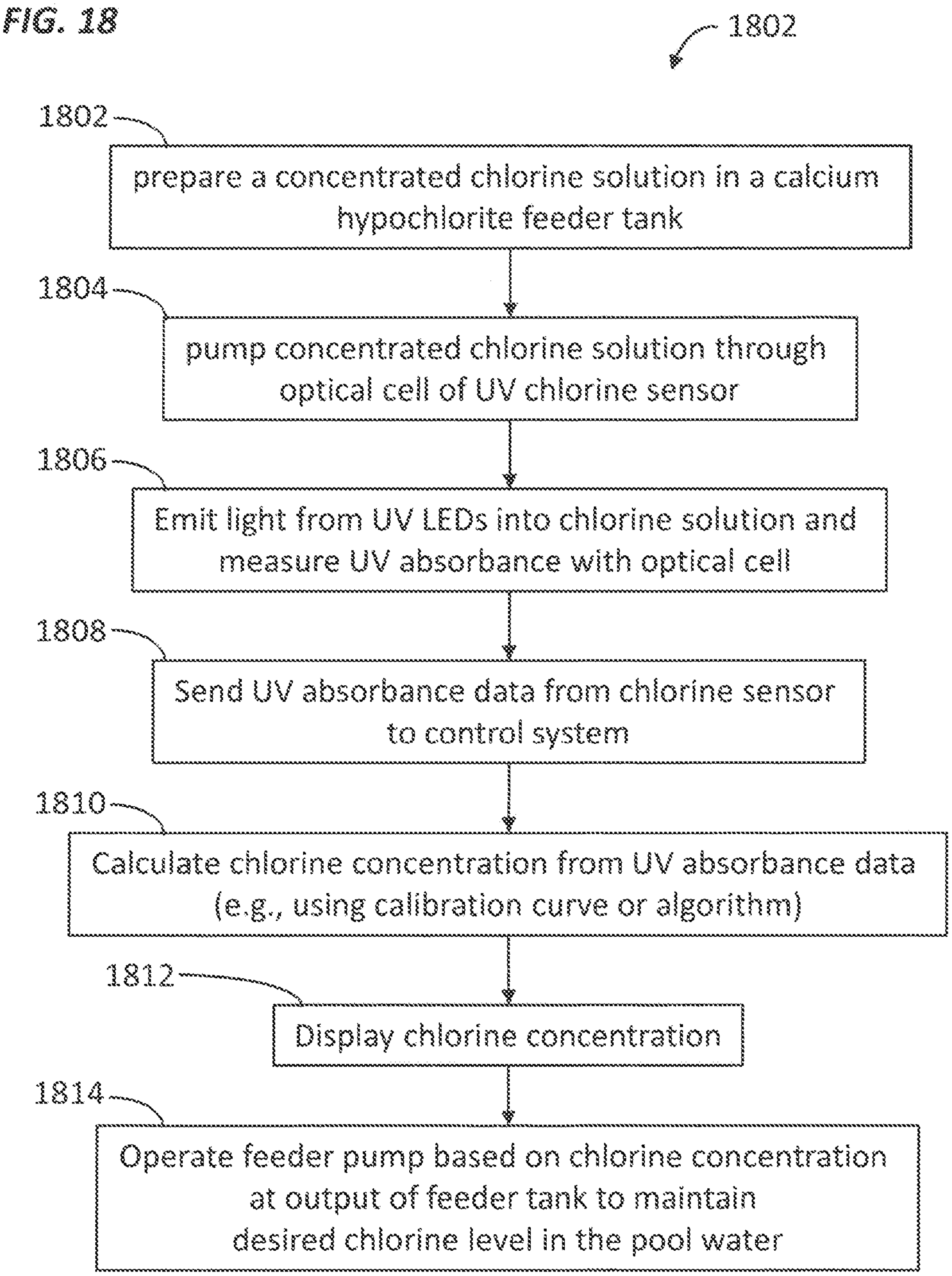
FIG. 18 is a flowchart showing steps of a method of monitoring and controlling water quality and conditions in a swimming pool according to some embodiments of this disclosure.

A method 1802 of operating a UV absorbance chlorine sensor according to this disclosure is described with reference to FIG. 18, and may, for example, involve some or all of the following steps:

Step 1802: The calcium hypochlorite feeder tank is configured to prepare and hold a concentrated chlorine solution with a target chlorine concentration of approximately 200 ppm.

Step 1804: The concentrated chlorine solution associated with the chlorine feeder system is moved through the optical cell of the UV absorbance chlorine sensor.

Step 1806: The UV LEDs of the UV absorbance chlorine sensor emit light into the concentrated chlorine solution as it moves through the optical cell, and the optical cell measures or detects the amount of UV absorbance.

Step 1808: The UV absorbance chlorine sensor sends the measured UV absorbance data to the control system.

Step 1810: The control system analyzes the data received and calculates or estimates the chlorine concentration based on the established calibration curve or via an algorithm or formula.

Step 1812: The chlorine concentration of the concentrated chlorine solution of the feeder system is displayed on a monitor or interface of the control system.

Step 1814: The control system controls or adjusts the operation of the feeder pump based on the measured chlorine concentration associated with the feeder system to maintain a desired chlorine level in the pool water of the pool system.

Thus, by monitoring the chlorine concentration associated with the calcium hypochlorite feeder system, the control system can provide more accurate dosing of concentrated chlorine solution into the pool water, and thereby provide more reliable control of the chlorine concentration of the pool water in the pool volume tank. Additionally, any deviations or abnormalities in the chlorine concentration of the chlorine feeder system can be detected more quickly, thereby allowing for timely adjustments and/or corrective actions.

Overall, the devices, systems, and methods described in this disclosure provide an efficient and cost-effective solution for monitoring concentrated chlorine solutions associated with a calcium hypochlorite feeder, to thereby facilitate more precise control of chlorine levels in the pool water.

Exemplary Embodiment of a UV Absorbance Chlorine Sensor:

In a particular embodiment of a UV absorbance chlorine sensor, UV LEDs having wavelengths of 275 nm and 365 nm were utilized. The UV LED at 365 nm was selected to function as a reference for calibration purposes. In some alternative embodiments, UV LEDs having wavelengths of 290 nm and 410 nm may be used. The optical cell portion of the UV absorbance chlorine sensor, which transmits UV light through the chlorine solution flowing therethrough, may be constructed using a chemically resistant plastic material, for example. Input tubing may be used to connect to either a peristaltic pump or directly to the optical cell. The output tubing from the optical cell may be connected to the pool fluidic system (e.g., via the main recirculation loop of the pool system), allowing the chlorine solution to be introduced into the circulation of pool water.

Figure 9A:
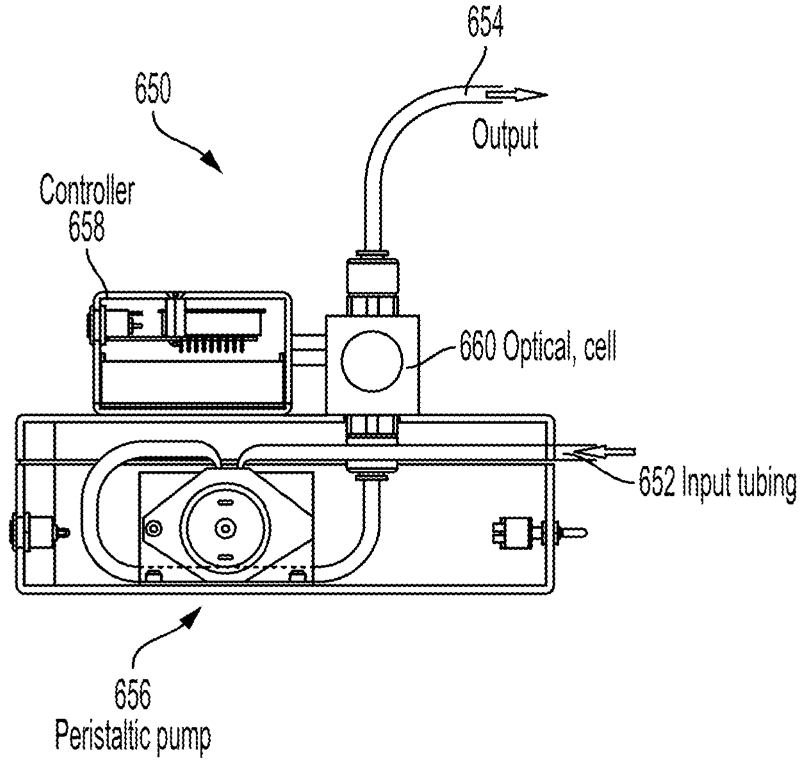
FIGS. 9A and 9B are front and top views, respectively, of an embodiment of an ultraviolet ("UV") sensor system for monitoring chlorine concentration associated with a chlorine feeder system for a swimming pool according to some embodiments of this disclosure.
Figure 9B:
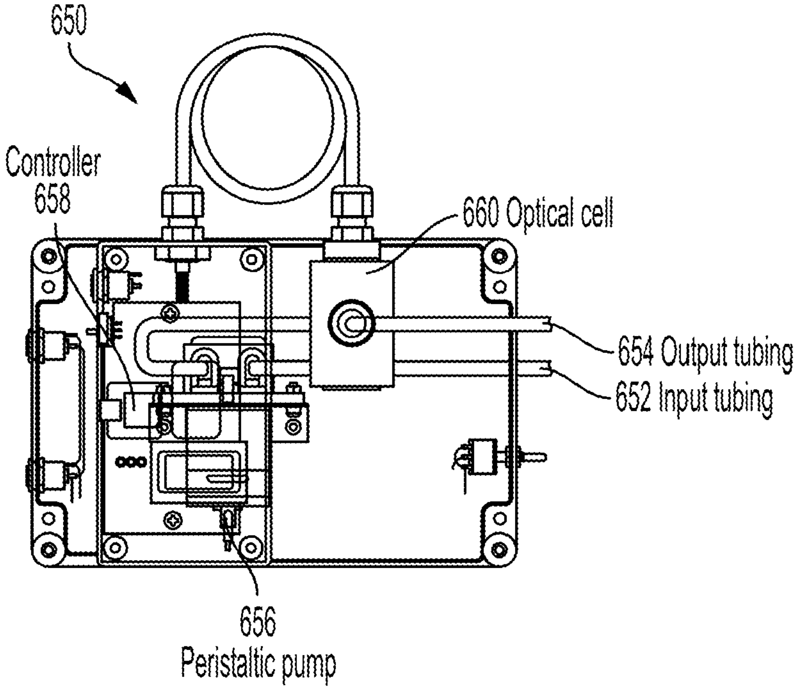

FIGS. 9A and 9B are front and top views, respectively, showing a UV absorbance chlorine sensor 650 according to this disclosure. UV absorbance chlorine sensor 650 may include input tubing 652, output tubing 654, a pump 656 (e.g., a peristaltic pump), an optical cell 660, and a controller 658, according to various embodiments. The input tubing 652 receives a concentrated chlorine solution associated with the chlorine feeder system (e.g., directly from the feeder tank, or at the output of the feeder pump, etc.) and directs it to the pump 656. Pump 656, which may be a peristaltic pump, for example, operates to cause the concentrated chlorine solution to flow through the optical cell 660. In some embodiments, the flow through the optical cell 660 is in an upward flow direction, as can be seen in FIG. 9A. The optical cell 660 functions to emit light from UV LEDs into and through the concentrated chlorine solution as it flows therethrough, and to detect light absorbance. Data regarding the light absorbance detected by optical cell 660 is sent to controller 658 where it can be evaluated and/or used to measure or estimate the chlorine concentration of the concentrated chlorine solution as it flows through the optical cell 660.

Figure 10A:
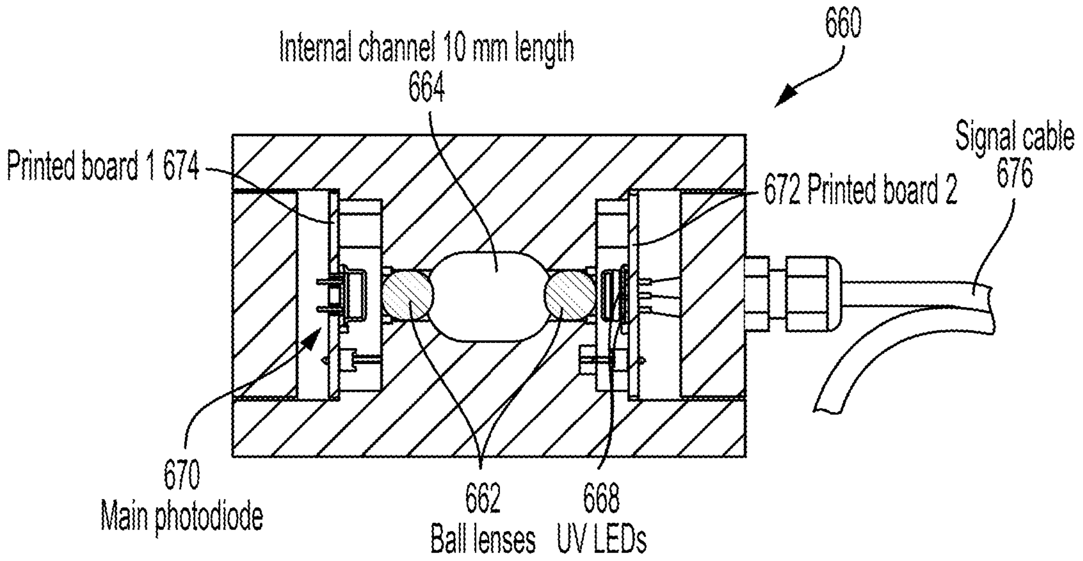
FIGS. 10A and 10B are front and top schematic cross-sectional views, respectively, of an embodiment of an ultraviolet ("UV") sensor system for monitoring chlorine concentration associated with a chlorine feeder system for a swimming pool according to some embodiments of this disclosure.
Figure 10B:
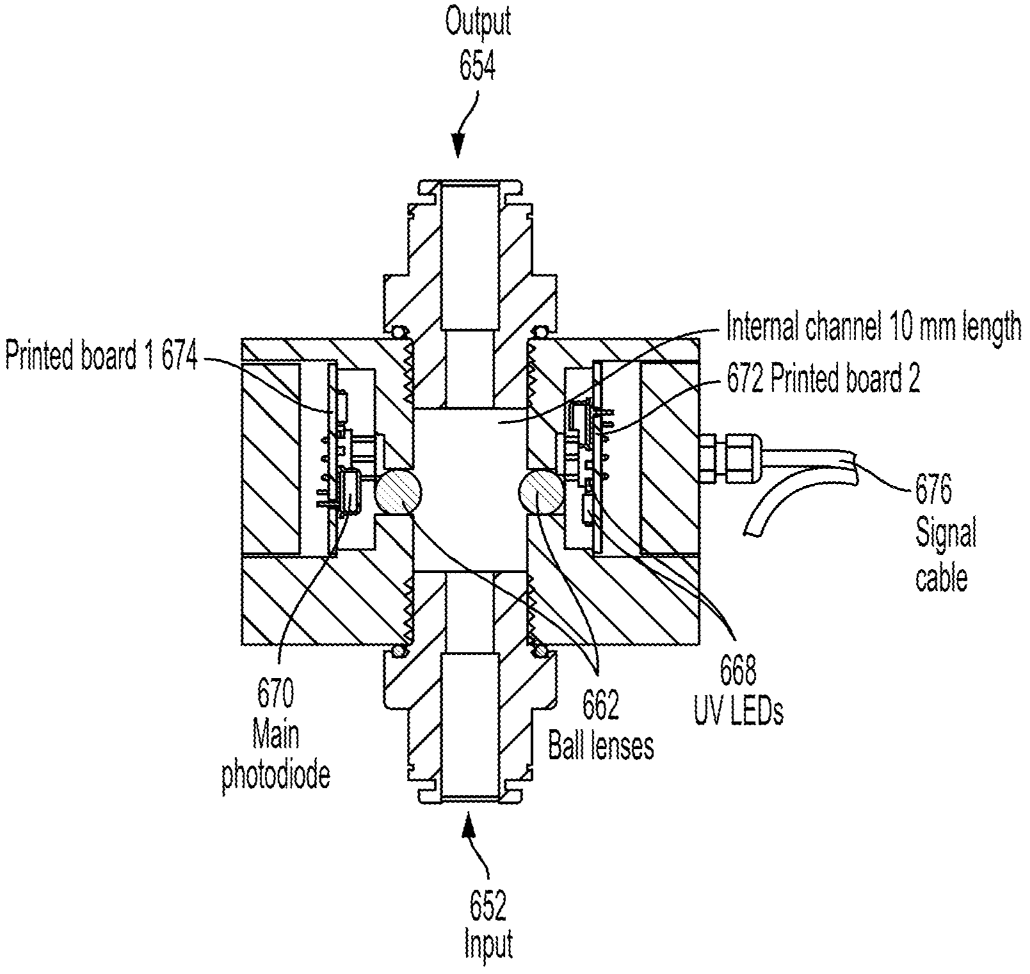

FIGS. 10A and 10B are front and top cross-sectional views, respectively, of optical cell 660 of UV absorbance chlorine sensor 650 according to certain embodiment of this disclosure. With reference to FIGS. 10A and 10B, optical cell 660 may comprise two sapphire ball lenses 662 positioned on opposite sides of an internal channel 664 configured to direct the concentrated chlorine solution to flow therethrough. As mentioned above with respect to FIG. 9A, the concentrated chlorine solution within the optical cell 660 may be directed to flow upwards through the internal channel 664 in order to facilitate removal of any potential bubbles that may otherwise form or become trapped inside the optical cell 660, thereby helping to ensure accurate UV absorbance measurements are made.

In some embodiments, the ball lenses 662 may be pressed into plastic channels having a smaller diameter than the lenses themselves, which may help ensure a reliable seal using relatively few parts. This may also prevent leakage of the concentrated chlorine solution at the UV absorbance sensor 650. FIGS. 10A and 10B also show an exemplary arrangement of UV LEDs 668 at one side of the internal channel 664 (adjacent one of the sapphire ball lenses 662). Note: Although two UV LEDs 668 are shown in FIGS. 10A and 10B, it is contemplated that a single UV LED could be employed in some embodiments, or more than two UV LEDs are employed, etc. At the opposite side of the internal channel 664 from the UV LEDs 668, a main photodiode 670 is positioned (adjacent the other of the sapphire ball lenses 662) to receive the UV light energy that has passed through the concentrated chlorine solution in the internal channel 664 in order to detect and/or estimate the light absorbance of the concentrated chlorine solution. Printed circuit boards 672, 674 may also be provided in order to process and/or generate suitable signals for generate the UV light signals and the UV absorbance measurements, respectively. A signal cable 676 is also shown for delivering energy (electrical energy and/or optical light energy according to various embodiments) for generating the UV LED light signals to the optical cell 660.

Figure 11:
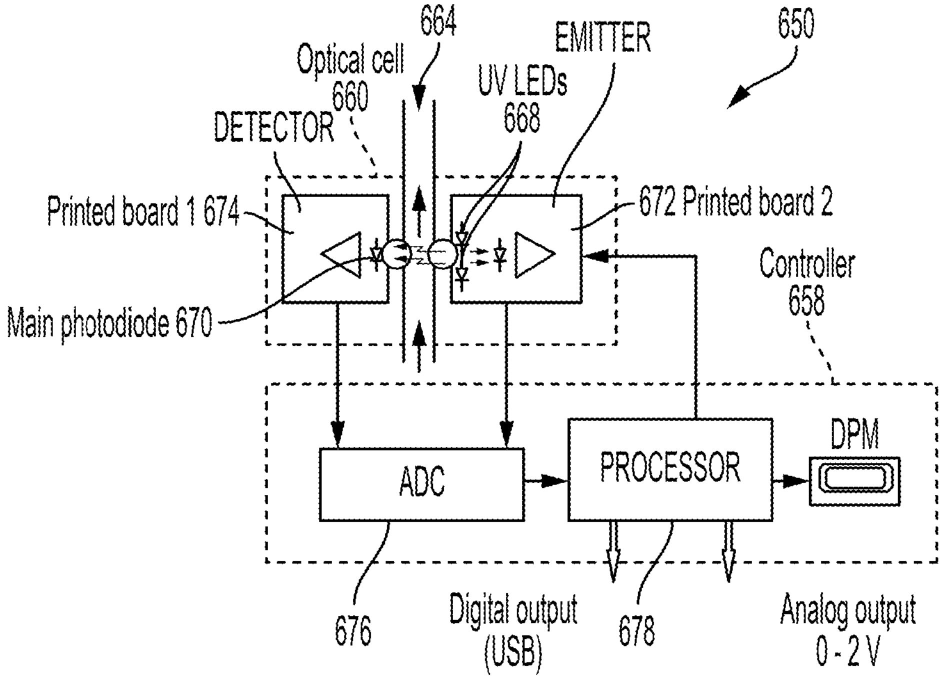
FIG. 11 is a schematic block diagram of a system for measuring the chlorine concentration associated with a chlorine feeder system for a swimming pool and using the information to control and/or maintain water quality in a swimming pool according to some embodiments of this disclosure.
Figure 12A:
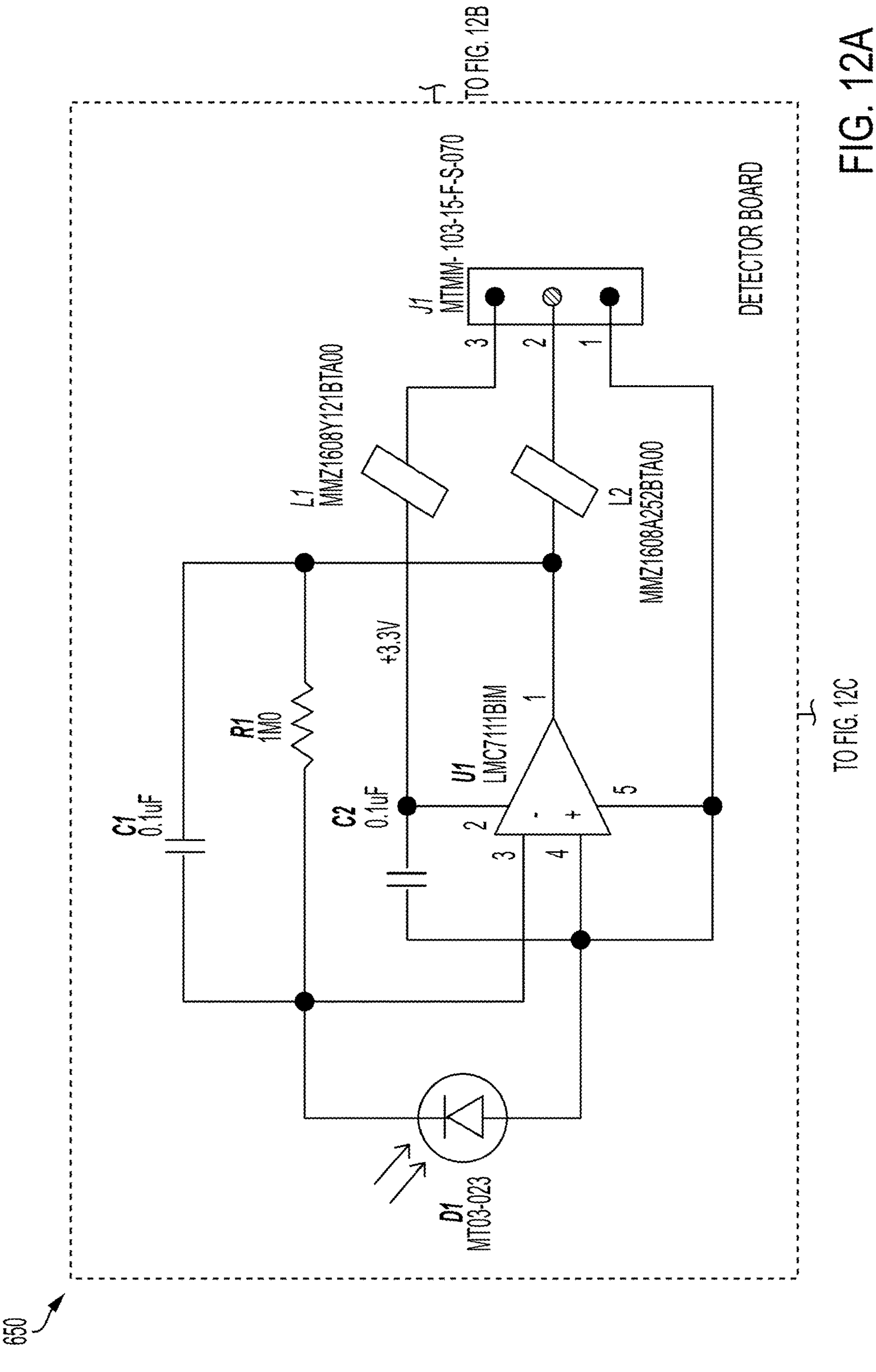
FIG. 12 is a detailed circuit diagram of a portion of a device for measuring chlorine concentration associated with a chlorine feeder system for a swimming pool according to some embodiments of this disclosure.
Figure 12B:
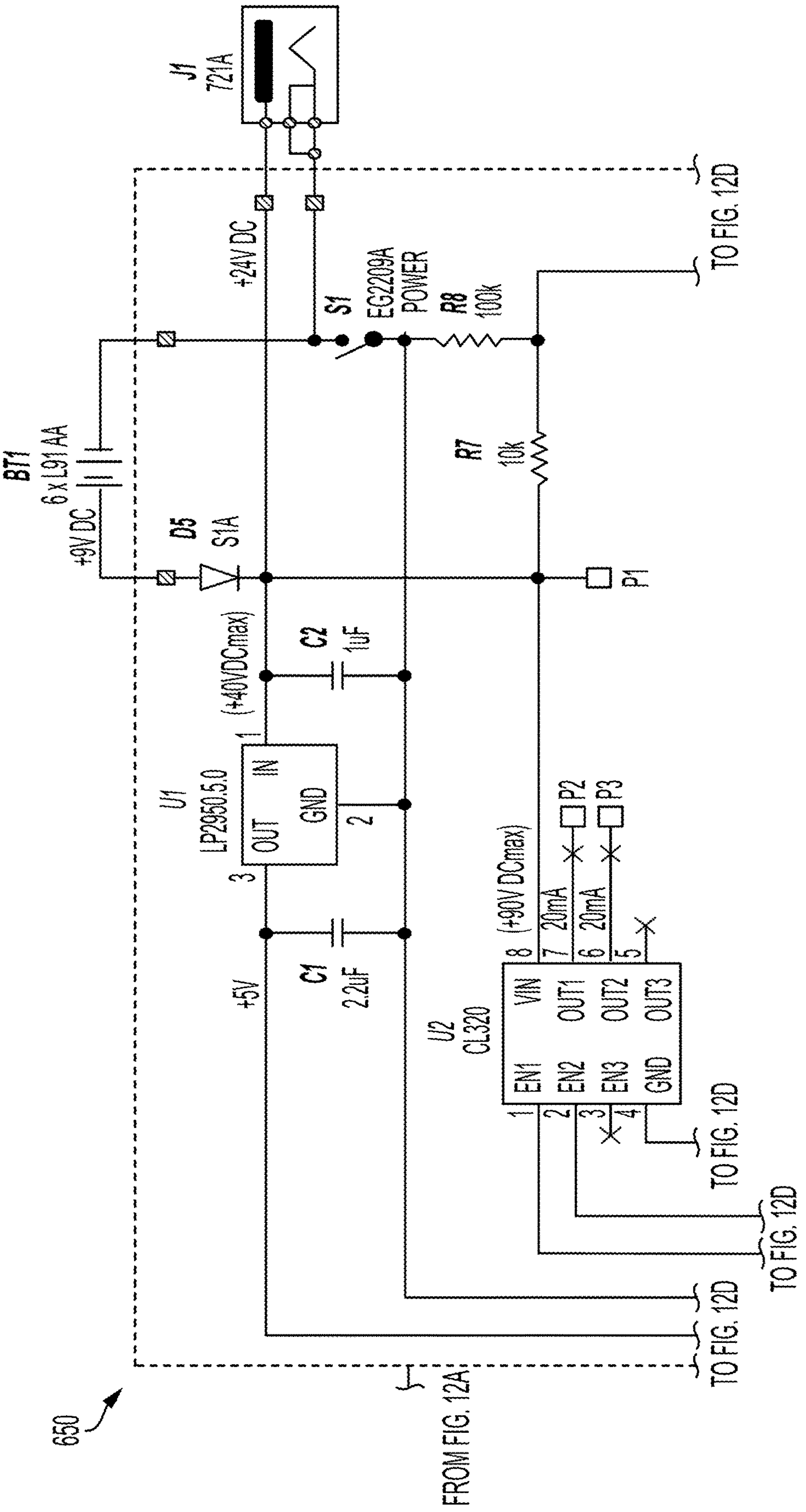
Figure 12C:
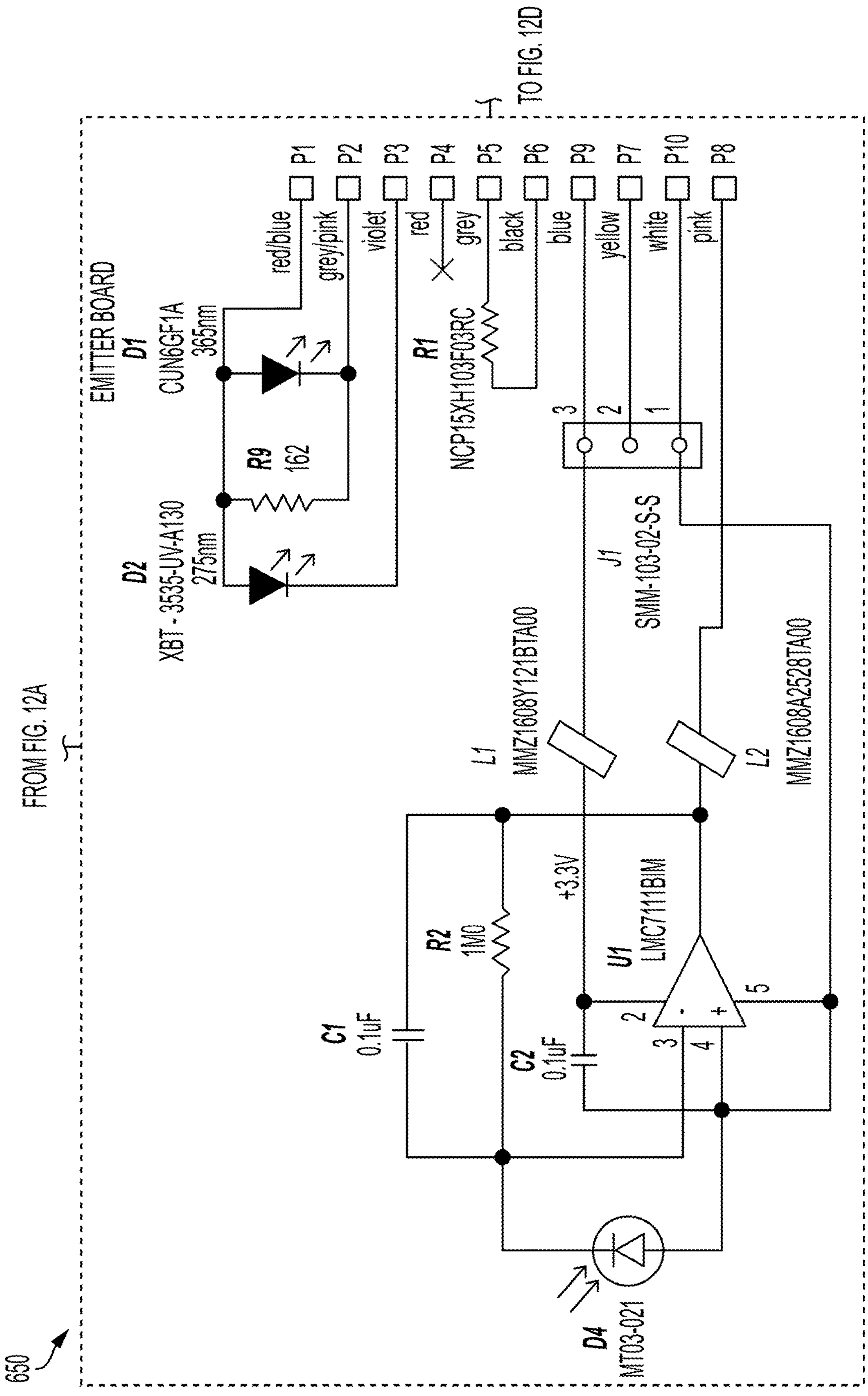
Figure 12D:
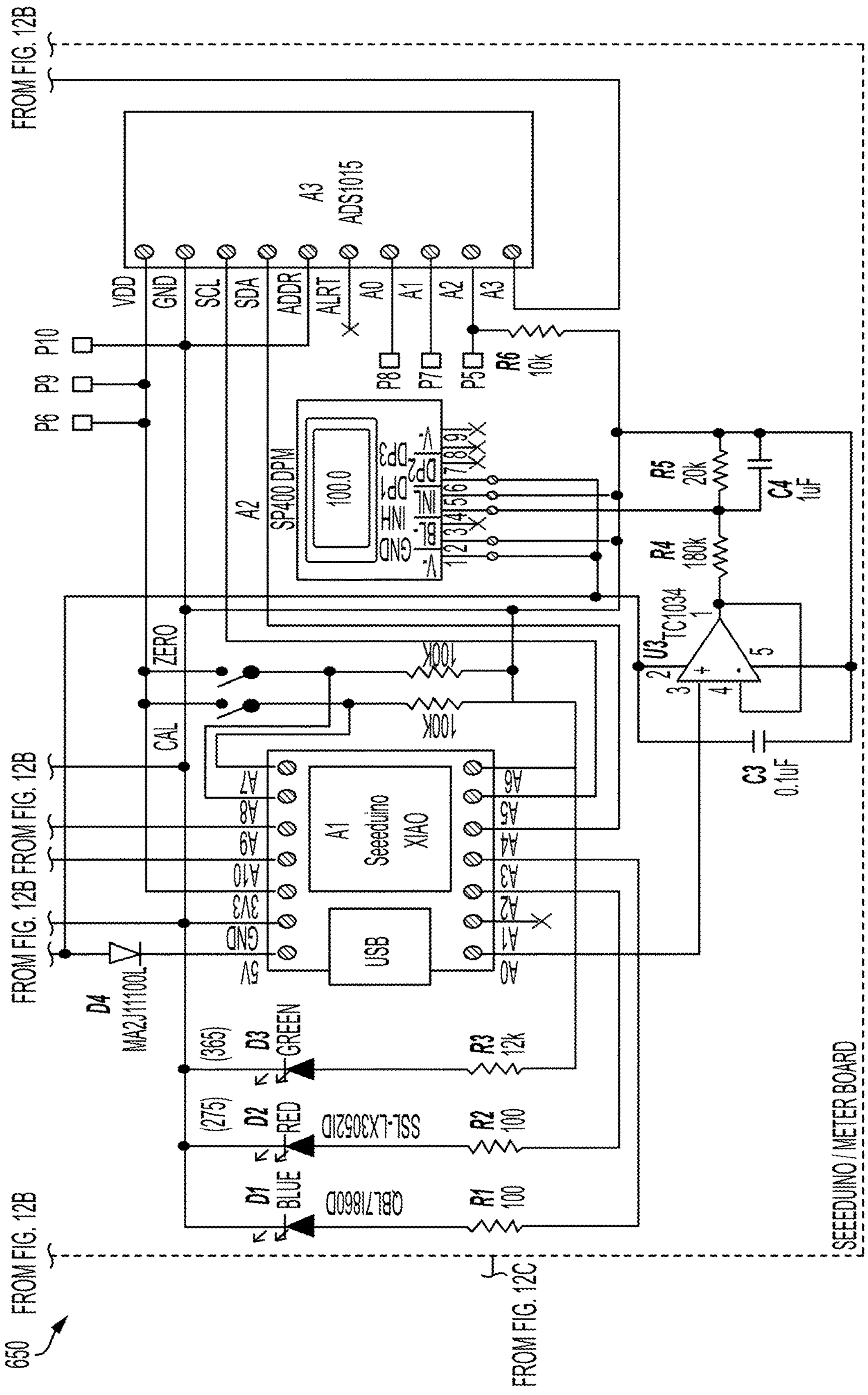

FIG. 11 is a block diagram of UV absorbance chlorine sensor 650, showing the main electrical components and typical signal flow paths of an embodiment of the UV absorbance chlorine sensor 650 according to this disclosure. For example, FIG. 11 shows optical cell 660 and controller 658 of UV absorbance chlorine sensor 650. Controller 658, for example, has processor 678 and an analog-to-digital converter ("ADC") 676. Processor 678 may send a signal to printed circuit board 672 of optical cell 660 in order to initiate or trigger the emission of UV light from one or more of the UV LEDs 668. UV LEDs 668 may be mounted on an emitter board within the optical cell 660, for example. In some embodiments, UV LEDs 668 having wavelengths of 275 nm and 365 nm may be utilized for chlorine concentration measurement. Processor 678 may be configured to manage the measuring cycle and the activation of the UV LEDs 668 in some embodiments. The processor 678 may also interface with ADC 676 to measure signals received from main photodiode 670 (and, in some embodiments, from a reference photodiode as well).

The main photodiode 670 may be located on the detector board within the optical cell 660 in some embodiments. Main photodiode 670 detects the UV light transmitted through the chlorine solution and produces an electrical signal proportional to the UV absorbance, which is indicative of the chlorine concentration of the chlorine solution. Main photodiode 670 of optical cell 660 may receive light energy emitted from the one or more of the UV LEDs 668 (after passing through fluid in the internal channel 664), and the received energy may result in a corresponding signal being generated and sent by printed circuit board 674 to ADC 676. ADC 676 may also receive a signal from printed circuit board 672 in conjunction with the emission of light energy from the UV LEDs (e.g., information regarding the light energy such as timing, wavelength, etc.). The ADC 676 may, as a result of the signals received from the optical cell 660, send a signal to processor 678 corresponding to a measured or detected chlorine concentration of the feeder system. The processor 678 may, in turn, use the signal corresponding to measured or detected chlorine concentration to communicate with other aspects of the pool system 100, for example, to control the operation of pumps, valves, sensors, controllers, etc.

In some embodiments, a reference photodiode (not shown in FIG. 11) may be positioned on the emitter board and may serve as a reference for calibration purposes. For example, by comparing signals from the main photodiode and reference photodiode for two UV wavelengths, accurate chlorine concentration measurements can be obtained, and errors or problems with the photodiodes may be detected and corrected for.

In some embodiments, a UV absorbance chlorine sensor may continuously measure the chlorine concentration of the fluid within the optical cell and may report the results through digital (e.g., USB) and analog outputs. This may facilitate integration of the UV absorbance chlorine sensor with the main controller of the pool water control system, allowing for improved monitoring and more rapid and precise control of chlorine levels in the pool water.

FIG. 12 is a detailed electrical schematic of an exemplary UV absorbance chlorine sensor 650 according to some embodiments of this disclosure. This may facilitate continuous (or near-continuous) measurements of the chlorine concentration of the solution flowing through the optical cell and reporting results through digital (USB) and analog outputs to the main controller of the pool controlling system.

Test Results for the UV Absorbance Chlorine Sensor

Figure 13:
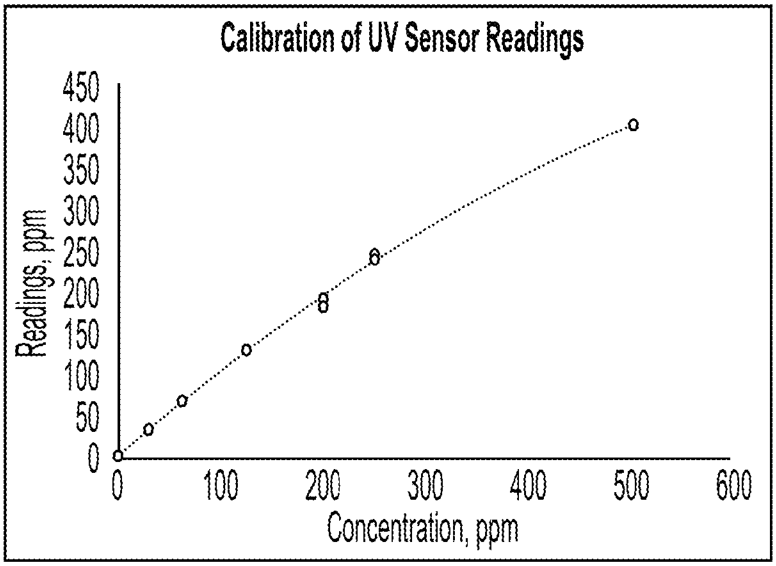
FIG. 13 is a plot of sensor readings of an exemplary UV chlorine sensor according to some embodiments of this disclosure, showing calibration/linearity of sensor readings versus known concentrations.

Solutions of calcium hypochlorite with different concentrations were prepared and measured with the UV absorbance chlorine sensor. FIG. 13 is a plot of chlorine sensor readings as measured with the UV absorbance chlorine sensor of this disclosure plotted against the known values of chlorine concentration. The plot of FIG. 13 shows strong agreement and linearity of readings versus "actuals," at least up to a concentration of about 250 ppm chlorine. This result shows that the proposed UV absorbance chlorine sensor will provide good results throughout the range of chlorine concentrations of interest.

Fluid Connections According to Option A

Figure 14:
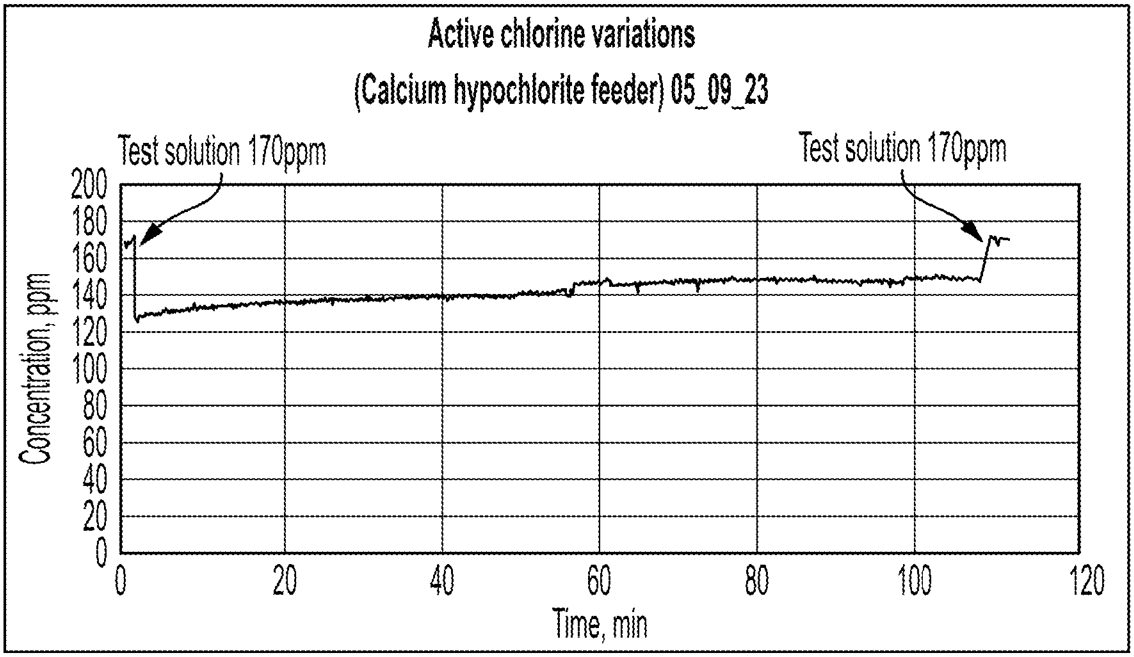
FIG. 14 is a plot of chlorine concentration vs. time associated with a calcium hypochlorite feeder tank of a swimming pool system according to some embodiments of this disclosure.

FIG. 14 is a plot of chlorine sensor readings as a function of time for the UV absorbance chlorine sensor 250 of Option A (corresponding to the pool system 200 of FIG. 2). As shown, the UV absorbance chlorine sensor 250 was connected to the feeder tank 212 with an additional pump 252 provided to circulate solution from the chlorine feeder tank 212 through the UV absorbance chlorine sensor 250 on a continuous (or near-continuous) basis. Based on the test results using the UV absorbance chlorine sensor 250 connected to the pool fluidic system 200 according to option A, the following observations were made:

Connection to Feeder Tank 212: The UV absorbance chlorine sensor 250 was successfully connected to the feeder tank 212, allowing for monitoring of the concentrated chlorine in the feeder tank 212. This setup provides valuable information about the chlorine concentration within the feeder tank 212.

Continuous Sample Renewal: The use of a peristaltic pump for pump 252 ensured a continuous flow of sample fluid through the UV absorbance chlorine sensor 250, allowing for real-time monitoring of chlorine concentration. This setup ensures that the sensor receives fresh samples for accurate measurements.

Chlorine Concentration Measurements: The chlorine sensor provided readings in the range of 130 ppm to 150 ppm, which is close to the allowed low level of 100 ppm in some installations. This indicates that the chlorine concentration in the feeder tank 212 is within the desired range. However, considering the deviation from the target concentration (e.g., 200 ppm), it may be recommended in this particular case to service or adjust the pumping time to ensure more precise control.

Verification with 170 ppm Solution: To assess the accuracy of the UV absorbance chlorine sensor 250, a 170 ppm solution was introduced (near the beginning and end portions of the test period), and the UV absorbance chlorine sensor 250 reported an appropriate value with less than about a 5 ppm error. This demonstrates the reliability of the UV absorbance chlorine sensor 250 in measuring higher chlorine concentrations (e.g., in the range of 100 ppm to 250 ppm) and its ability to provide accurate readings in this range.

Figure 15:
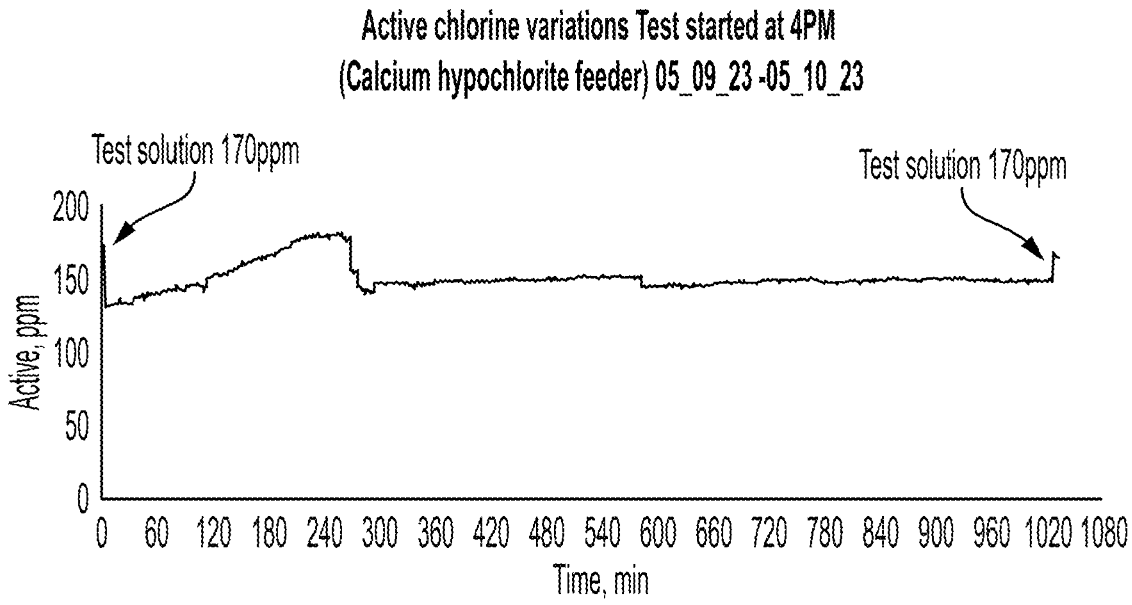
FIG. 15 is a plot of chlorine concentration vs. time associated with a calcium hypochlorite feeder tank of a swimming pool system according to some embodiments of this disclosure.

FIG. 15 provides a plot of chlorine sensor readings from a UV absorbance chlorine sensor in another similar test performed for a longer period of time after certain adjustments were made. Notably, after a 4 hour period in which the chlorine concentration of the feeder tank 212 became more stable and delivered a concentrated chlorine solution with concentration of 150 ppm, as was expected in this test.

It is evident that the UV absorbance chlorine sensor 250 connected to the pool fluidic system 200 according to Option A (FIG. 2) is effective in measuring and monitoring the chlorine concentration of the concentrated chlorine solution in the feeder tank 212. The UV absorbance chlorine sensor 250 provided valuable data for maintaining the desired chlorine levels in the pool water and highlights the need for adjustment or servicing to provide more precise control of chlorine concentration in the pool water.

Fluid Connections According to Option B

Figure 16:
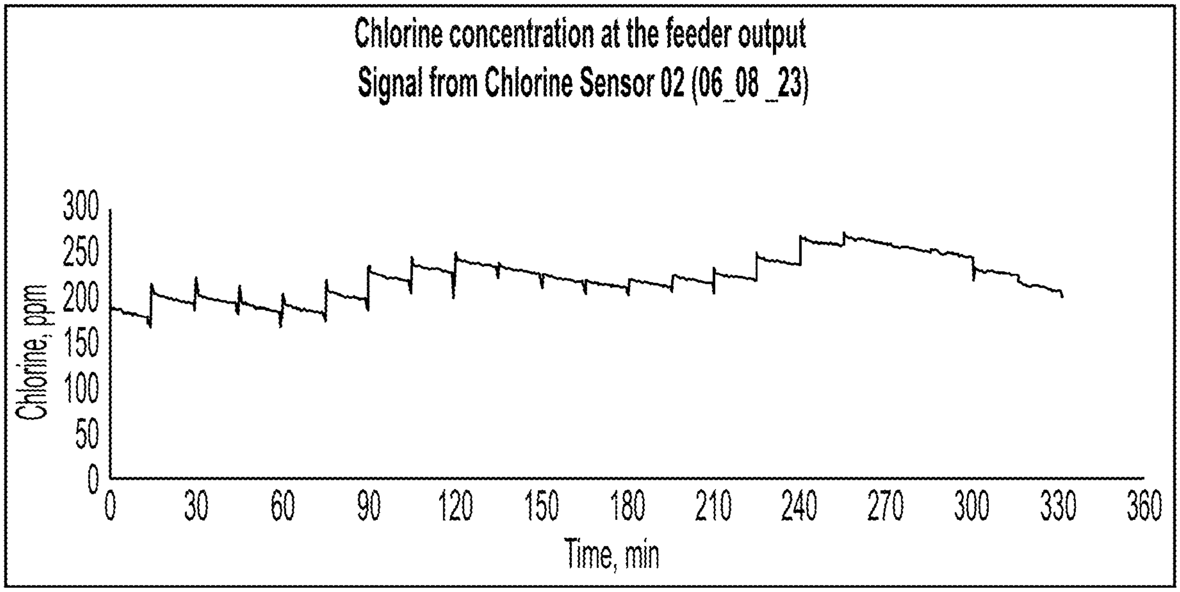
FIG. 16 is a plot of chlorine concentration vs. time associated with a calcium hypochlorite feeder tank of a swimming pool system according to some embodiments of this disclosure.

FIG. 16 is a plot of chlorine sensor readings as a function of time for the UV absorbance chlorine sensor 350 of Option B (corresponding to the pool system 300 of FIG. 4) in which the UV absorbance chlorine sensor 350 was connected at the output of the feeder pump 314.

Based on the test results using the UV absorbance chlorine sensor 350 fluidly connected to the pool fluidic system 300 according to option B, the following observations were made:

Connection to Feeder Pump 314: The UV absorbance chlorine sensor 350 was successfully connected at the output of the feeder pump 314. This setup allows for monitoring the chlorine concentration in the chlorine solution actually delivered by the pump 314.

Absence of Flow Sensor: In this specific test setup, no flow sensor was used to indicate when a new sample was delivered. The feeder pump 314 was activated every 15 minutes, delivering the concentrated chlorine solution into the pool fluidic system 300 and simultaneously delivering a new sample for measurement. However, it was observed that the sample degraded over time when the pump 314 was not activated. This degradation indicates that a flow sensor could be beneficial in providing accurate timing for when a new sample is delivered, ensuring that the UV absorbance chlorine sensor 350 measures the actual concentrated chlorine solution from the feeder pump delivery line.

Sample Degradation: During the 15-minute intervals between pump activations, visible degradation of the sensor readings was observed. This degradation suggests that without a flow sensor, the UV absorbance chlorine sensor 350 may not be consistently measuring fresh samples, which may potentially lead to inaccurate readings using this setup.

Based on these test results, it is evident that the UV absorbance chlorine sensor 350 connected to the pool fluidic system 300 according to option B might benefit from the inclusion of a flow sensor. The flow sensor would provide a reliable indication of when a new sample is delivered, ensuring that the chlorine sensor measures the actual chlorine solution from the feeder delivery line. This would enhance the accuracy of the chlorine concentration measurements and may prevent sample degradation over time.

In some exemplary embodiments, a pool fluidic system according to this disclosure may comprise some or all of the following components: a pool basin for holding pool water; a main pump for circulating the pool water through the system; a filter for removing impurities from the pool water; a heater for adjusting the temperature of the pool water; a sensor manifold including a pH sensor and a low concentration chlorine sensor for monitoring the pH level and chlorine concentration in the pool water; an acid pump for regulating the pH level in the pool water; a calcium hypochlorite feeder system comprising a feeder tank and a feeder pump for dispensing a concentrated chlorine solution into the pool water; a UV absorbance high concentration chlorine sensor in fluidic communication with either the feeder tank or the feeder output line for monitoring the chlorine concentration in the feeder tank or the chlorine solution output from the feeder pump.

In some embodiments, the pool fluidic system may further include a controller for receiving and processing sensor data from the pH sensor, the low concentration chlorine sensor, and the UV absorbance high concentration chlorine sensor, and controlling the operation of the main pump, filter, heater, acid pump, feeder pump, and UV absorbance high concentration chlorine sensor based on the received sensor data.

In some embodiments, the pool fluidic system may have the sensor manifold positioned to receive samples from the main circulation loop of the pool water.

In some embodiments, the pool fluidic system may further include the UV absorbance high concentration chlorine sensor having UV LEDs as light sources and sapphire ball lenses as material for an optical cell.

In some embodiments, the pool fluidic system may further include the feeder pump being activated by the controller based on the chlorine concentration readings from the UV absorbance high concentration chlorine sensor in order to maintain the desired chlorine level in the pool water.

In some embodiments, the pool fluidic system may further include the controller being configured to detect an abnormality in the feeder system operation based on the chlorine concentration readings from the UV absorbance high concentration chlorine sensor, including out of product events, feeder pump malfunctioning, and clogged lines or obstructions in the feeder connections.

In some embodiments, the pool fluidic system may further include the controller being configured to adjust the operation of the acid pump based on the pH readings from the pH sensor to maintain the desired pH level in the pool water.

In some embodiments, the pool fluidic system may further include the UV absorbance high concentration chlorine sensor being connected to the feeder tank via an input tubing and an output tubing, allowing for continuous monitoring of the chlorine concentration in the feeder tank. In some embodiments, the pool fluidic system further comprises a pump to deliver fluid samples from the feeder system to the UV absorbance high concentration chlorine sensor.

In some embodiments, the pool fluidic system may further include the UV absorbance high concentration chlorine sensor being connected at the output of the feeder pump.

In some embodiments, the pool fluidic system may further include the calcium hypochlorite feeder system being connected to the main recirculation loop before the heater, the UV absorbance high concentration chlorine sensor being connected at the output of the feeder pump via an input tubing, and an output tubing being connected to the main recirculation loop after the heater.

In some embodiments, the pool fluidic system further comprises a flow sensor in fluidic communication with the UV absorbance high concentration chlorine sensor, providing an indication of when a new sample is delivered from the feeder pump to the UV absorbance high concentration chlorine sensor. In some embodiments, the pool fluidic system further includes the flow sensor being configured to activate the UV absorbance high concentration chlorine sensor for measuring the chlorine concentration in the chlorine solution delivered by the feeder pump.

In some embodiments, the pool fluidic system further comprises an electromechanical valve, wherein a first input of the electromechanical valve is connected to the output of the feeder pump, a second input is connected to the output of the sensor manifold, and an output of the electromechanical valve is connected to the input tubing of the UV absorbance high concentration chlorine sensor, and the output tubing of the UV absorbance high concentration chlorine sensor is connected to the main fluidic system after the heater.

In some embodiments, the pool fluidic system further comprises a mixing manifold, wherein the output of the feeder pump is mixed with the flow from the sensor manifold, wherein the input tubing of the UV absorbance high concentration chlorine sensor is connected to the mixing manifold, and wherein the output tubing of the UV absorbance high concentration chlorine sensor is connected to the main fluidic system after the heater.

In some embodiments, the pool fluidic system further comprises an adjustment valve, wherein the adjustment valve is placed after the mixing manifold, between the input tubing and the output tubing of the UV absorbance high concentration chlorine sensor.

What is claimed is:

1. A system for controlling water conditions in a swimming pool, the system comprising:

a pool basin for holding a volume of pool water;

a main circulation pump for drawing the pool water from the pool basin, delivering the pool water drawn from the pool basin to a conditioning system via a main recirculation line, and returning the pool water to the pool basin, wherein the conditioning system includes:

a filter for removing impurities from the pool water;

a chlorine sensor for monitoring a chlorine concentration of the pool water;

a chlorine feeder system comprising a feeder tank and a feeder pump, the feeder pump configured to deliver a concentrated chlorine solution from the feeder tank to be added to the pool water via the main recirculation line and returned to the pool basin; and an ultraviolet ("UV") absorbance chlorine sensor for monitoring a chlorine concentration of the concentrated chlorine solution of the chlorine feeder system, wherein the UV absorbance chlorine sensor is configured to measure higher chlorine concentrations than the chlorine sensor for monitoring the chlorine concentration of the pool water.

2. The system of claim 1, further comprising a controller, the controller configured to receive first sensor data from the chlorine sensor regarding the chlorine concentration of the pool water and receive second sensor data from the UV absorbance sensor regarding the chlorine concentration of the concentrated chlorine solution of the chlorine feeder system, the controller further configured to control operation of one or more of the main circulation pump and the feeder pump in response to the received first sensor data and second sensor data.

3. The system of claim 2, wherein the conditioning system includes a sensor manifold comprising the chlorine sensor for monitoring the chlorine concentration of the pool water and a pH sensor for monitoring a pH level of the pool water.

4. The system of claim 3, wherein the conditioning system further includes an acid pump for delivering an acidic solution to the pool water to regulate the pH level of the pool water, wherein the controller is configured to receive third sensor data from the pH sensor regarding the pH level of the pool water, and wherein the controller is configured to control operation of the acid pump in response to the received third sensor data.

5. The system of claim 4, wherein the conditioning system further includes a mixing manifold, the mixing manifold having a first input fluidly connected to an output from the feeder pump, the mixing manifold having an output fluidly connected to the main recirculation line for returning the pool water to the pool basin.

6. The system of claim 5, wherein the sensor manifold is fluidly connected to an input fluidic line positioned to sample the pool water, the input fluidic line comprising a check valve, the sensor manifold having an output line fluidly connected to a second input of the mixing manifold, wherein an output of the acid pump is fluidly connected to the output of the mixing manifold, and wherein the UV absorbance chlorine sensor has an output fluidly connected between the input and the output of the mixing manifold.

7. The system of claim 2, wherein the concentrated chlorine solution in the feeder tank is a calcium hypochlorite solution.

8. The system of claim 2, wherein the UV absorbance chlorine sensor is in fluidic communication with the feeder tank to monitor the chlorine concentration of the chlorine feeder system.

9. The system of claim 2, wherein the UV absorbance chlorine sensor is in fluidic communication with an output from the feeder pump to monitor the chlorine concentration of the chlorine feeder system.

10. The system of claim 2, wherein the UV absorbance chlorine sensor comprises one or more UV light-emitting diodes ("LEDs") configured to emit light into the concentrated chlorine solution.

11. The system of claim 10, wherein the one or more UV LEDs emit light within a range of wavelengths from 260 nm to 320 nm.

12. The system of claim 10, wherein the UV absorbance chlorine sensor further comprises two sapphire ball lenses disposed adjacent a fluid path of the concentrated chlorine solution through the UV absorbance chlorine sensor.

13. The system of claim 2, wherein the controller is configured to control operation of the feeder pump to maintain the chlorine concentration of the pool water within a range of 1 ppm to 8 ppm chlorine.

14. The system of claim 13, wherein the controller is configured to control operation of the feeder pump to maintain the chlorine concentration of the pool water within a range of 4 ppm to 6 ppm chlorine.

15. The system of claim 2, wherein the controller is configured to detect one or more abnormalities with the chlorine feeder system based on chlorine concentration readings from the UV absorbance chlorine sensor.

16. The system of claim 15, wherein the one or more abnormalities with the chlorine feeder system includes one or more of: an out of product event, the feeder pump malfunctioning, a clogged line, and an obstruction in the chlorine feeder system.

17. The system of claim 2, wherein the UV absorbance chlorine sensor is connected to the feeder tank via an input tubing, an output tubing, and a pump, thereby facilitating continuous monitoring of chlorine concentration in the feeder tank.

18. The system of claim 2, wherein an input of the UV absorbance chlorine sensor is connected at an output of the feeder pump via an input tubing, and an output from the UV absorbance chlorine sensor is connected to the feeder tank via an output tubing.

19. A system for controlling water conditions in a swimming pool, the system comprising:

a pool basin for holding a volume of pool water;

a main circulation pump for drawing the pool water from the pool basin, delivering the pool water drawn from the pool basin to a conditioning system via a main recirculation line, and returning the pool water to the pool basin, wherein the conditioning system includes:

a filter for removing impurities from the pool water;

a sensor manifold fluidly connected to an input fluidic line configured to sample the pool water drawn from the pool basin, the sensor manifold including a chlorine sensor for monitoring a chlorine concentration of the pool water;

a chlorine feeder system comprising a feeder tank and a feeder pump, the feeder pump configured to deliver a concentrated chlorine solution from the feeder tank to be added to the pool water via the main recirculation line and returned to the pool basin;

an ultraviolet ("UV") absorbance chlorine sensor for monitoring a chlorine concentration of the concentrated chlorine solution in the feeder tank; and a mixing manifold, the mixing manifold having a first input fluidly connected to an output from the feeder pump, the mixing manifold having an output fluidly connected to the main recirculation line for returning the pool water to the pool basin, the input of the mixing manifold being fluidly connected to an output line of the sensor manifold, and a controller, the controller configured to receive first sensor data from the chlorine sensor regarding the chlorine concentration of the pool water and receive second sensor data from the UV absorbance sensor regarding the chlorine concentration of the concentrated chlorine solution of the chlorine feeder system, the controller further configured to control operation of the main circulation pump and the feeder pump in response to the received first sensor data and the received second sensor data.

20. The system of claim 19, wherein the sensor manifold further comprises a pH sensor for monitoring a pH level of the pool water drawn from the pool basin, wherein the conditioning system further includes an acid pump for delivering an acidic solution to the pool water to regulate the pH level of the pool water, wherein the controller is configured to receive third sensor data from the pH sensor regarding the pH level of the pool water, and wherein the controller is configured to control operation of the acid pump in response to the received third sensor data.

* * * * *